United States Patent
Freissmuth et al.

(10) Patent No.: US 10,226,465 B2
(45) Date of Patent: Mar. 12, 2019

(54) COMPOSITION FOR USE IN INCREASING ENGRAFTMENT EFFICACY OF HAEMATOPOETIC STEM CELLS AFTER TRANSPLANTATION

(71) Applicant: SCIPHARM SÀRL, Luxembourg (LU)

(72) Inventors: Michael Freissmuth, Vienna (AT); Eva-Maria Zebedin-Brandl, Vienna (AT); Zahra Kazemi, Vienna (AT)

(73) Assignee: SCIPHARM SÀRL, Luxembourg (LU)

( * ) Notice: Subject to any disclaimer, the term of this patent is extended or adjusted under 35 U.S.C. 154(b) by 0 days.

(21) Appl. No.: 15/547,059

(22) PCT Filed: Jan. 27, 2016

(86) PCT No.: PCT/EP2016/051672
§ 371 (c)(1),
(2) Date: Jul. 27, 2017

(87) PCT Pub. No.: WO2016/120310
PCT Pub. Date: Aug. 4, 2016

(65) Prior Publication Data
US 2018/0008606 A1  Jan. 11, 2018

(30) Foreign Application Priority Data

Jan. 27, 2015  (EP) .................... 15152664

(51) Int. Cl.
| A61K 31/40 | (2006.01) |
| A61K 35/12 | (2015.01) |
| A61K 35/28 | (2015.01) |
| C12N 5/077 | (2010.01) |
| A61K 31/403 | (2006.01) |
| A61K 31/497 | (2006.01) |
| A61K 31/506 | (2006.01) |
| A61K 31/519 | (2006.01) |
| A61K 31/522 | (2006.01) |
| C12N 5/0789 | (2010.01) |

(52) U.S. Cl.
CPC ............ *A61K 31/519* (2013.01); *A61K 31/40* (2013.01); *A61K 31/403* (2013.01); *A61K 31/497* (2013.01); *A61K 31/506* (2013.01); *A61K 31/522* (2013.01); *A61K 35/28* (2013.01); *C12N 5/0647* (2013.01); *C12N 5/0669* (2013.01); *A61K 2035/124* (2013.01); *C12N 2501/01* (2013.01); *C12N 2501/02* (2013.01); *C12N 2501/734* (2013.01)

(58) Field of Classification Search
CPC ........ A61K 31/40; A61K 31/12; A61K 31/28; A61K 31/497; A61K 31/506; A61K 31/519; A61K 31/522
See application file for complete search history.

(56) References Cited

U.S. PATENT DOCUMENTS

| 2004/0247574 A1* | 12/2004 | Christopherson, II ....................... C12N 5/0647 424/93.7 |
| 2008/0085264 A1 | 4/2008 | Christopherson, II et al. |
| 2010/0247491 A1* | 9/2010 | Westenfelder ......... A61K 31/40 424/93.7 |
| 2011/0091429 A1 | 4/2011 | Christopherson, II et al. |
| 2014/0288010 A1 | 9/2014 | Hill et al. |

FOREIGN PATENT DOCUMENTS

| WO | 2007/041368 A2 | 4/2007 |
| WO | WO 2007/041368 * | 4/2007 |
| WO | 2009/152186 A1 | 12/2009 |
| WO | 2012074676 A2 | 6/2012 |
| WO | 2012/095511 A1 | 7/2012 |

OTHER PUBLICATIONS

Adams et al, "Hematopoietic stem cells depend upon Gsa-mediated signalling to engraft bone marrow" (2009) Nature 459:103-107.
Aksentijevich et al, "Chemotherapy and bone marrow reserve: lessons learned from autologous stem cell transplantation" (2002) Cancer Biother Radiopharm 17:399-403.
Awedan, A.A. "High intensity regimens with autologous hematopoietic stem cell transplantation as treatment of multiple myeloma" (2002) Ann Transplant 7:38-43.
Broxmeyer et al, "inhibition of DPP4/CD26 and dmPGE2 treatment enhances engraftment of mouse bone marrow hematopoietic stem cells," 2014, Blood Cells, Molecules and Diseases 53:34-38.
Broxmeyer et al, "Background and Future Considerations for Human Cord Blood Hematopoietic Cell Transplantation, Including Economic Concerns" Stem Cells and Development, 2013, vol. 22, suppl. 1, pp. 103-110.
Christopherson II, Kent "Modulation of Hematopoietic Stem Cell Homing and Engraftment by CD26", Science, 2004, vol. 305, No. 5686, pp. 1000-1003.
De Mendizabal et al, "MOdelling the Sitagliptin Effect on Dipeptidyl Peptidase-4 Activity in Adulta with Haematological Malignancies After Umbilical Cord Blood Haematopoietic Cell Transplantation" Clin Pharmacokinet, 2014, vol. 53, pp. 247-259.
Dexter et al, "Inhibitors of cholera toxin-induced adenosine diphosphate ribosylation of membrane-associated proteins block stem cell differentiation" (1985) Blood 65:1544-1548.
Freissmuth et al, "Mutations of Gsa designed to alter the reactivity of the protein with bacterial toxins. Substitutions at ARG187 result in loss of GTPase activity", (1989) J Biol Chem 264:21907-21914.
Goessling et al, "Genetic interaction of PGE2 and Wnt signaling regulates developmental specification of stem cells and regeneration" (2009) Cell 136:1136-1147.

(Continued)

*Primary Examiner* — Shirley V Gembeh
(74) *Attorney, Agent, or Firm* — Loza & Loza, LLP; Michael F. Fedrick

(57) ABSTRACT

The present invention provides the new use of composition comprising at least one inhibitor of dipeptidyl peptidase IV (DPP-IV) for increasing migration and homing of haematopoetic progenitor cells in stem cell transplanted recipients, wherein said haematopoetic stem and/or progenitor cells had been treated in vitro with an engraftment enhancing compound, specifically with a prostacyclin analog and a cAMP enhancer before transplantation.

13 Claims, 15 Drawing Sheets

Figure 1:
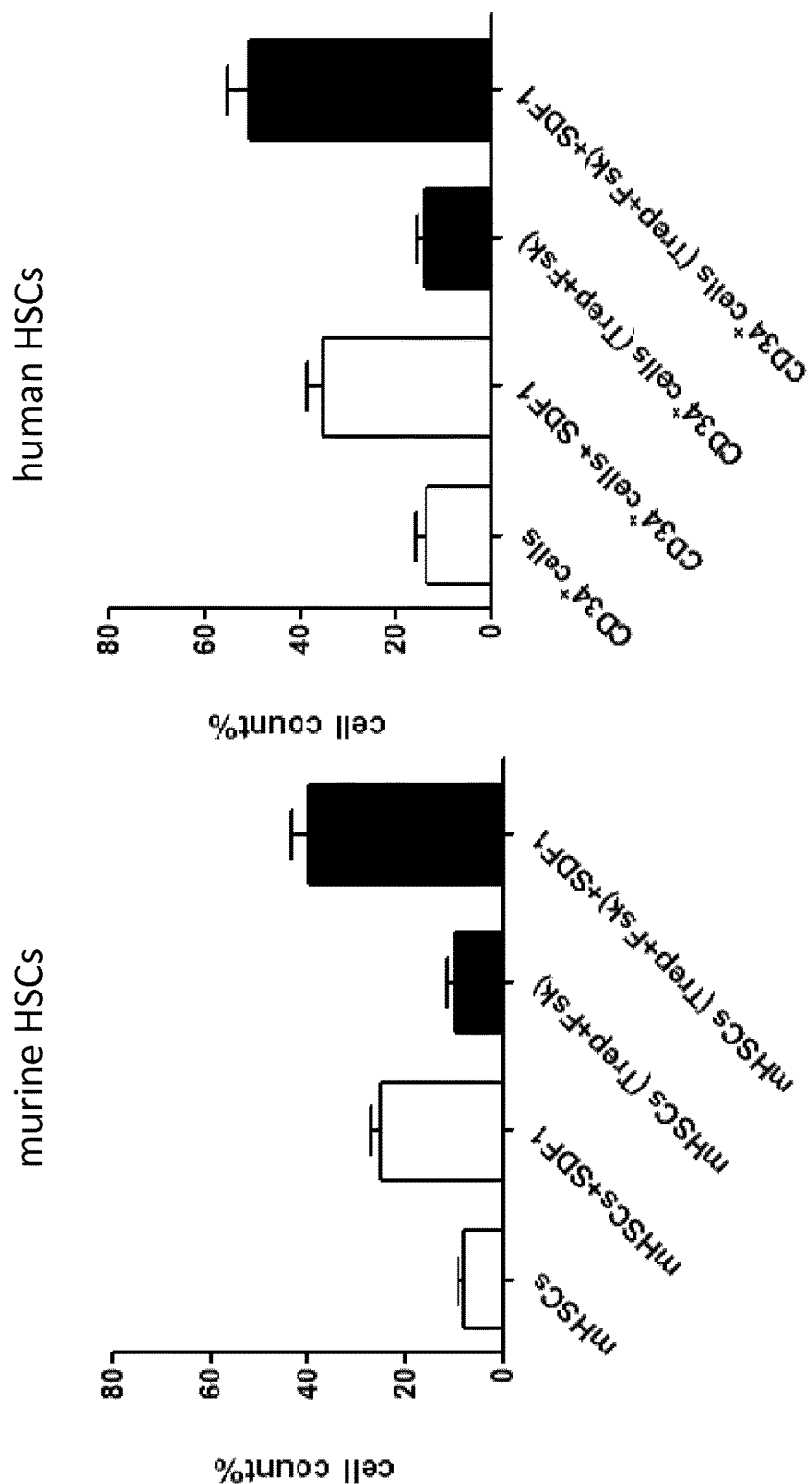

Specification includes a Sequence Listing.

(56) References Cited

OTHER PUBLICATIONS

Hoggatt et al, "Prostaglandin E2 enhances hematopoietic stem cell homing, survival, and proliferation", Blood, 2009, vol. 113, No. 22, pp. 5444-5455.
Hussain et al, "Treprostinil stimulates the engraftment of haematopoetic stem cells" BMC Pharmacology, vol. 11, No. Suppl 2, 2011, p. A6.
Kucia et al, "Trafficking of Normal Stem Cells and Metastasis of Cancer Stem Cells Involve Similar Mechanisms: Pivotal Role of the SDF-1-CXCR4 Axe" Stem Cells, 2005, 23:879-894.
Long et al, "Cholera toxin and phorbol diesters synergistically modulate murine hematopoietic progenitor cell proliferation" (1988) Exp Hematol. 16:195-200.
North et al, "Prostaglandin E2 regulates vertebrate haematopoietic stem cell homeostasis", (2007) Nature 447:1007-1011.
Ponsioen et al, "Detecting cAMP-induced Epac activation by fluorescence resonance energy transfer: Epac as a novel cAMP indicator", EMBO Reports (2004) 5(12):1176-1180.
Schwaiger et al, "Dipeptidyl peptidase IV (DPPIV/CD26) inhibition does not improve engraftment of unfractionated syngeneic or allogeneic bone marrow after nonmyeloablative conditioning" Experimental Hematology, 2011, vol. 40, No. 2, pp. 97-106.
International Search Report for PCT/EP16/51672 dated Mar. 31, 2016; 5 pages.
Written Opinion for PCT/EP16/1672 dated Mar. 31, 2016; 7 pages.
Extended European Search Report for EP Application No. 15152664.7 dated Jul. 16, 2015; 8 pages.
Peranteau, W.H., et al., "CD26 inhibition enhances allogeneic donor-cell homing and engraftment after in utero hemalopoietic-cell transplantation," Blood, 2006, vol. 108, No. 13, pp. 4268-4274.
Yoo et al., "Loss of CD26 Protease Activity in Recipient Mice during Hematopoietic Stem Cell Transplantation Results in Improved Transplant Efficiency," Transfusion, 2013, vol. 53, No. 4, pp. 878-887.
Search Report in corresponding Singapore Patent Application No. 11201705812S dated Jul. 5, 2018.
Written Opinion in corresponding Singapore Patent Application No. 11201705812S dated Jul. 5, 2018.

* cited by examiner

SEQUENCE LISTING

<160> NUMBER OF SEQ ID NOS: 28

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
gagagccagg gcgcagt                                                    17

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gcaagggctc atgtcagg                                                   18

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
agcaggagcc aagttccag                                                  19

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
catccgctag gctcaggtta                                                20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccacctcatt ctcctggcta                                                20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tttcctttcg ggaagaggtt                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ttatgaccat caccttcgcc                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
taaaaaccga agagctcgga                                                20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agcgaccatt tggaaagatg                                                20

<210> SEQ ID NO 10
<211> LENGTH: 20
<212> TYPE: DNA
<213> ORGANISM: Artificial Sequence
<220> FEATURE:
```

```
<223> OTHER INFORMATION: Primer

<400> SEQUENCE: 10
tgatgtgatc ctggcagaaa                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tggatccctg ggtttatctg                                              20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gggaaacagg tactgcaatg a                                            21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttactcattg ccacctccct                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cgctccaaac ttggctgata                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tctctggtgg tgctcatctg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgcaaatctg ggtttctgct                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aggaagctgt tggctgaaaa                                                 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ctcactgacg ttggcaaaga                                                 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aggtgcaggt agcagtgacc                                                 20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
actcacactg atcggttcca                                                 20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
gggcacgaga ggatgaagt                                                  19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gatggcctga gtgaagcct                                                  19

<210> SEQ ID NO 23
<211> LENGTH: 18
<212> TYPE: DNA
<213> ORGANISM: Artificial Sequence
<220> FEATURE:
<223> OTHER INFORMATION: Primer
```

```
<400> SEQUENCE: 23
gtgtgctccc tgcctctc                                                    18

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
ggggttgaag gcgtagaag                                                   19

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aaggctccat agtacgcacg                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ctcagactac aggcacgggt                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
cggaggtctt ctgcttcttc                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cactatgtgt tctctgcccg                                                  20
```

COMPOSITION FOR USE IN INCREASING ENGRAFTMENT EFFICACY OF HAEMATOPOETIC STEM CELLS AFTER TRANSPLANTATION

CROSS-REFERENCE TO RELATED APPLICATIONS

This application is the U.S. national stage of International Patent Application No. PCT/EP2016/051672, filed on Jan. 27, 2016 and entitled COMPOSITION FOR USE IN INCREASING ENGRAFTMENT EFFICACY OF HAEMATOPOETIC STEM CELLS AFTER TRANSPLANTATION, which claims the benefit of priority under 35 U.S.C. § 119 from European Patent Application No. 15152664.7, filed Jan. 27, 2015. The disclosures of the foregoing applications are incorporated herein by reference in their entirety.

SEQUENCE LISTING

The entire content of a Sequence Listing titled "Sequence_Listing.txt," created on Jun. 30, 2017 and having a size of 6 kilobytes, which has been submitted in electronic form in connection with the present application, is hereby incorporated by reference herein in its entirety.

FIELD OF THE INVENTION

The present invention provides the new use of composition comprising at least one inhibitor of dipeptidyl peptidase IV (DPP-IV) for increasing migration and homing of haematopoetic progenitor cells in stem cell transplanted recipients, wherein said haematopoetic progenitor cells had been treated in vitro before transplantation of said cells with a prostacyclin analogue for enhancing the engraftment of said progenitor cells. Specifically, pretreatment is performed with prostacyclin analogue and a cAMP enhancer before transplantation.

Haematopoetic stem cells (HSCs) are primitive cells capable of regenerating all blood products throughout the life of an individual, balancing their self-renewal with progeny differentiation. HSCs undergo transition in location during development and circulate in mammals throughout life, moving into and out of the bloodstream to engage bone marrow niches in sequential steps of homing and engraftment. Homing is the process by which the donor stem cells find their way to the bone marrow, engrafting of stem cells means their growth in bone marrow.

HSCs have therapeutic potential as a result of their capacity to restore blood and immune cells in transplant recipients. Furthermore, HSCs have the potential to generate cells for other tissues such as brain, muscle and liver. Human autologous and allogeneic bone marrow transplantation methods are currently used as therapies for diseases such as leukemia, lymphoma, and other life-threatening diseases. Autologous bone marrow transplantation is a standard procedure that is used to increase the therapeutic window of cytotoxic drugs and thus to allow for high dose intensity chemotherapy (Aksentijevich I, Flinn I (2002) Chemotherapy and bone marrow reserve: lessons learned from autologous stem cell transplantation. *Cancer Biother Radiopharm* 17:399-403, Awedan A A (2002) High intensity regimens with autologous hematopoetic stem cell transplantation as treatment of multiple myeloma. *Ann Transplant* 7:38-43) For these procedures, however, a large amount of donor bone marrow must be isolated to ensure that there are enough HSCs for engraftment.

Cell trafficking, specifically homing of HSCs is regulated by several different intracellular mechanisms.

First, the need of a $G\alpha_s$-transduced signal in vivo to populate the bone marrow niche by HSCs is described (Adams G B et al., (2009) Haematopoietic stem cells depend on Gαs-mediated signaling to engraft bone marrow. *Nature* 459:103-107). These findings confirm earlier in vitro experiments, which showed that the activation of $G\alpha_s$ promotes the survival and differentiation of haematopoetic stem cells (Dexter T M et al., (1985) Inhibitors of cholera toxin-induced adenosine diphosphate ribosylation of membrane-associated proteins block stem cell differentiation. *Blood* 65:1544-1548, Long M W et al., (1988) Cholera toxin and phorbol diesters synergistically modulate murine hematopoietic progenitor cell proliferation *Exp Hematol.* 16:195-200). $G\alpha_s$ is the guanine nucleotide binding α-subunit of the heterotrimeric G protein that stimulates all 9 isoforms of membrane-bound mammalian adenylyl cyclase. $G\alpha_s$ can be constitutively activated ex vivo/in vitro by treating the cells with cholera toxin. This is because cholera toxin APD-ribosylates the catalytic arginine residue ($R^{186/187/201/202}$, the precise number of the arginine depends on the splice variant of $G\alpha_s$); an intact arginine residue is required for GTP-hydrolysis and the resulting deactivation of $G\alpha_s$ (Freissmuth M, Gilman A G (1989) Mutations of Gsα designed to alter the reactivity of the protein with bacterial toxins. Substitutions at $ARG^{187}$ result in loss of GTPase activity. *J Biol Chem* 264:21907-21914). Enhanced engraftment can indeed be observed after pretreatment of haematopoetic stem cells with cholera toxin: there were about twice as many ($Lin^-$) precursor cells in the bone marrow, if the stem cell preparation had been pretreated with cholera toxin (Adams, 2009). Second, HSCs express all four prostaglandin E receptors (EP1-4). The pretreatment of haematopoetic stem cells with (dimethylated) prostaglandin E2 enhances their engraftment (North T E, et al., (2007) Prostaglandin E2 regulates vertebrate haematopoietic stem cell homeostasis. *Nature* 447:1007-1011, 8; Hoggatt J, et al., (2009) Prostaglandin E2 enhances hematopoietic stem cell homing, survival, and proliferation (*Blood* 113:5444-5455). This effect is mediated by canonical $G\alpha_s$-dependent signalling, because the cAMP-induced activation of protein kinase A (PKA) synergizes with Wnt-dependent signals to stabilize β-catenin (Goessling W et al. (2009) Genetic interaction of PGE2 and Wnt signaling regulates developmental specification of stem cells and regeneration. *Cell* 136:1136-1147).

In addition, PGE2 also increases HSC CXCR4 mRNA and surface expression, enhances their migration to stromal cell derived factor-1 (SDF-1) in vitro and homing to bone marrow in vivo and stimulates HSC entry into and progression through cell cycle.

A method for enhancing engraftment of HSCs using a prostacyclin analogue, optionally in combination with forskolin, is described in WO2012/095511.

The SDF-1-CXCR4 axis is also known to be involved in cell homing. SDF-1 plays a pivotal role in the regulation of trafficking of normal HSCs and their homing and retention in the bone marrow (Kucia et al., Stem Cells, 2005).

According to WO2009/152186 A1, inhibition of CD26 peptidase (DPPIV, dipeptidylpeptidase IV) activity can enhance the migration activity and the use of CD26 peptidase inhibitors is described to enhance homing and engraftment of cells.

WO 2012/074676 describes a composition for liver preservation containing a GLP-1 antagonist and a DPPIV-Inhibitor.

Hussain Filza et al. report the effect of Treprostinil on stem cell transplantation (BMC Pharmacology, vol 11, no. Suppl 2, 2011, p A6).

US 2008/085264 discloses the use of a DPP-IV inhibitor/CD26 peptidase inhibitor for pretreatment to increase the transplantation efficacy of hematopoetic stem cell.

Broxmeyer H. et al. provide a survey on transplantation with hematopoetic stem cells. (STEM CELLS AND DEVELOPMENT, 2013, vol. 22, suppl. 1, pp. 103-110) and further discuss the use of dmPGE2 in combination with sitagliptin (Broxmeyer H. and Pelus, L. 2014, Blood Cells, Molecules and Diseases 53, 34-38).

Schwaiger E. et al. disclose the use of DPP-IV inhibitors and disclose that the presence of these inhibitors do not the engraftment of bone marrow (Experimental Hematology, 2011, vol. 40, no. 2, pp. 97-106).

Hoggatt J. et al. report the use of PGE2 for stimulating hematopoetic stem cells (BLOOD, 2009, vol. 113, no. 22, pp. 5444-5455).

WO2012/095511 describes the treatment of haematopoetic stem cells with Treprostinil and forskolin.

The localization of stem cells following transplantation is a critical determinant for a successful transplantation. At present, high numbers of stem cells are needed for transplantation because stem cells are not easily engrafted in the bone marrow and there is a long period of bone marrow aplasia leading to a decrease of mature blood cells.

It is thus still a need to provide methods and treatment regimens to efficiently stimulate HSCs to increase homing, engraftment and retention of isolated HSCs to bone marrow niches of subjects undergoing bone marrow transplantations and to reduce the number of HSCs needed for transplantation.

BRIEF DESCRIPTION OF THE INVENTION

The problem is solved by the embodiments of the present invention.

It has been surprisingly shown that haematopoetic stem cell homing and engraftment can be successfully increased by ex vivo pretreating said stem and/or progenitor cells with a prostacyclin analogue stimulating the engraftment properties of said cells and further administrating an inhibitor of dipeptidyl peptidase IV (DPP-IV) to the individual who was transplanted with said haematopoetic stem cells.

Specifically, it has been shown by the inventors that haematopoetic stem cell homing and engraftment can be successfully increased by ex vivo pretreating said cells with a combination of at least one prostacyclin analogue and at least one cAMP enhancer and further administrating an inhibitor of dipeptidyl peptidase IV (DPP-IV) to the individual who was transplanted with said haematopoetic stem cells.

Specifically, a composition is provided by the invention comprising at least one inhibitor of dipeptidyl peptidase IV (DPP-IV) for use in the treatment of haematopoetic stem cell transplanted recipients, wherein said haematopoetic stem cells had been treated in vitro, specifically with a prostacyclin analogue and a cAMP enhancer before transplantation.

Specifically, the invention provides a composition comprising at least one inhibitor of dipeptidyl peptidase IV (DPP-IV) for use in the treatment of haematopoetic stem cell transplanted recipients, wherein said recipients are transplanted with haematopoetic stem cells that had been treated in vitro with a prostacyclin analogue and optionally a cAMP enhancer to enhance engraftment.

The invention surprisingly showed that incubating isolated haematopoetic stem cells prior to transplantation, with a prostacyclin analogue, optionally together with a cAMP enhancer like forskolin, and administration of a DPP-IV inhibitor shortly before and after transplantation of said cells into a patient in need thereof highly increase HSC homing and engraftment efficiency. This is surprising because the inhibition of DPP-IV (by a gliptin) does per se not suffice to enhance bone marrow transplantation in murine models (Schwaiger E, et al., Exp Hematol. 2012 February; 40(2): 97-106. doi: 10.1016/j.exphem.2011.10.010).

According to a preferred embodiment, the haematopoetic stem cells are incubated with a combination of a prostacyclin analogue and a compound capable of elevating cAMP further, specifically forskolin or an inhibitor of cAMP degradation (phosphodiesterase inhibitor).

Further it was surprisingly shown by the inventors in an in vivo animal model, that administration of a DPP-IV inhibitor, specifically of vildagliptin, after transplantation of said cells significantly increases the survival rate of said haematopoetic cell recipients compared to an administration of a prostacyclin analogue.

It was further shown by the inventors that a combined administration of a prostacyclin analogue, specifically Treprostinil, and a DPP-IV inhibitor, specifically vildagliptin, after transplantation with Treprostinil and forskolin pretreated haematopoetic stem cells are mutually antagonistic.

According to an embodiment of the invention, said composition for use contains a DPP-IV inhibitor that is selected from gliptins, more specifically from the group consisting of sitagliptin, vildagliptin, alogliptin, saxagliptin, linagliptin, anagliptin, teneligliptin, gemigliptin and dutogliptin or functional analogues thereof.

According to a specific embodiment of the invention, the haematopoetic stem cells are incubated in vitro with a prostacyclin analogue which is selected from the group of Treprostinil, Iloprost, Cicaprost and Beraprost or pharmaceutically acceptable salts thereof, specifically said prostacyclin analogue is a derivative of Treprostinil, selected from the group of acid derivatives of Treprostinil, prodrugs of Treprostinil, polymorphs of Treprostinil or isomers of Treprostinil and anhydrous polymorphs of Treprostinil.

According to the embodiment, the pretreatment of haematopoetic stem cells is further in the presence of a cAMP enhancer, specifically of forskolin.

The present invention covers the use of a DPP-IV inhibitor in the treatment of a selected group of individuals, i.e. individuals suffering from bone marrow disease or from bone marrow related disease, specifically the bone marrow disease is leukemia, myelodysplastic syndrome, myeloproliferative disorders, aplastic anemia, sickle cell disease, a defect of the blood cell compartment, bone marrow diseases induced by chemotherapy or irradiation who undergo stem cell transplantation using haematopoetic stem cell samples which had been pretreated in vitro with a prostacyclin analogue and a cAMP inhibitor before transplantation.

More specifically, the defect of the blood cell compartment can be, but is not limited to haemoglobinopathy or a defect in neutrophil granulocyte function, a defect in T- and/or B-lymphocytes (e.g., severe combined immunodeficiency, Bruton's agammaglobulinemia).

According to a specific embodiment of the invention, individuals who are administered prostacyclin analogues after transplantation are not included in the group of individuals to be treated with a DPP-IV inhibitor.

According to an embodiment of the invention, the DPP-IV inhibitor is vildagliptin and wherein the haematopoetic stem cells had been treated in vitro with Treprostinil and forskolin before transplantation.

According to a further embodiment, the DPP-IV inhibitor is administered at least 5, specifically at least 10, specifically at least 15, specifically at least 24 hours before haematopoetic stem cell transplantation.

Administration of the DPP-IV inhibitor can be for a period needed for sufficient stem cell engraftment in the bone marrow.

The embodiment of the present invention also covers administering the DPP-IV inhibitor for at least 1 day, at least 2 days, at least 3 days, at least 4 days, at least 5 days, at least 6 days, at least 7 days, at least 8 days, at least 9 days, preferably for at least 10 days, preferably for at least 14 days after bone marrow transplantation.

According to the invention, the composition can be administered by intravenous or subcutaneous administration, or in an orally available form selected from the group of sustained release forms, tablets and capsules.

The invention also provides a method for enhancing the engraftment capabilities of haematopoetic cells comprising the sequential steps of
a) providing a sample of haematopoetic stem and/or progenitor cells,
b) administering an effective amount of a prostacyclin analogue enhancing engraftment to said cells,
c) incubating said mixture for a period of time sufficient to stimulate G $alpha_s$-signaling in said cells,
d) isolating said cells
e) transplanting said cells into an individual in need thereof
f) administering to said individual an effective amount of a DPP-IV inhibitor.

The invention specifically provides a method for enhancing the engraftment capabilities of haematopoetic cells comprising the sequential steps of
a) providing a sample of haematopoetic cells,
b) administering an effective amount of a prostacyclin analogue and a cAMP enhancer enhancing engraftment to said cells,
c) incubating said mixture for a period of time sufficient to stimulate G $alpha^s$-signaling in said cells,
d) isolating said cells
e) transplanting said cells into an individual in need thereof
f) administering to said individual an effective amount of a DPP-IV inhibitor.

The invention also provides a method wherein said stem cells are derived from cord blood, donor bone marrow or placenta.

The invention also provides a method for increasing the numbers of haematopoetic cells which are engrafted in the bone marrow after transplantation comprising the steps of in vitro contacting haematopoetic cells with an effective amount of a prostacyclin analogue specifically of Treprostinil, specifically together with a cAMP enhancer, specifically forskolin, administering the pre-incubated cells into an individual in need thereof and further administrating a DPP-IV inhibitor, specifically vildagliptin, to said individual shortly before and/or after administration of the haematopoetic cells.

According to a further embodiment of the invention, a method for enhancing engraftment of haematopoetic stem cells (HSCs) by an ex vivo pretreatment of the HSCs is provided, which comprises following steps:

a) providing a sample containing haematopoetic stem and/or progenitor cells,
b) admixing to said sample a composition comprising a prostacyclin analogue for increasing engraftment capabilities of the stem and/or progenitor cells, specifically comprising a prostacyclin analogue and a cAMP enhancer to obtain a mixture,
c) incubating said mixture for a period of time sufficient to stimulate G $alpha_s$ signaling in said cells,
d) isolating said stimulated cells,
e) transplanting said cells into an individual
f) administering a DPP-IV inhibitor to said individual, specifically be intravenous administration.

The invention also provides a kit of parts comprising
a) an amount of at least one prostacyclin analogue and forskolin in a first unit dosage form,
b) an amount of at least one DPP-IV inhibitor selected from gliptin,
in the form of two, three, four or more separate units of components a) and b), specifically for use in the treatment of a bone marrow disease, specifically the bone marrow disease is leukemia, a defect of the blood cell compartment and bone marrow diseases induced by chemotherapy or irradiation.

FIGURES

FIG. 1: Preincubation of murine and human haematopoietic stem and progenitor cells in the presence of Treprostinil and forskolin increases their migration towards SDF-1/CXCL12

Figure 2:
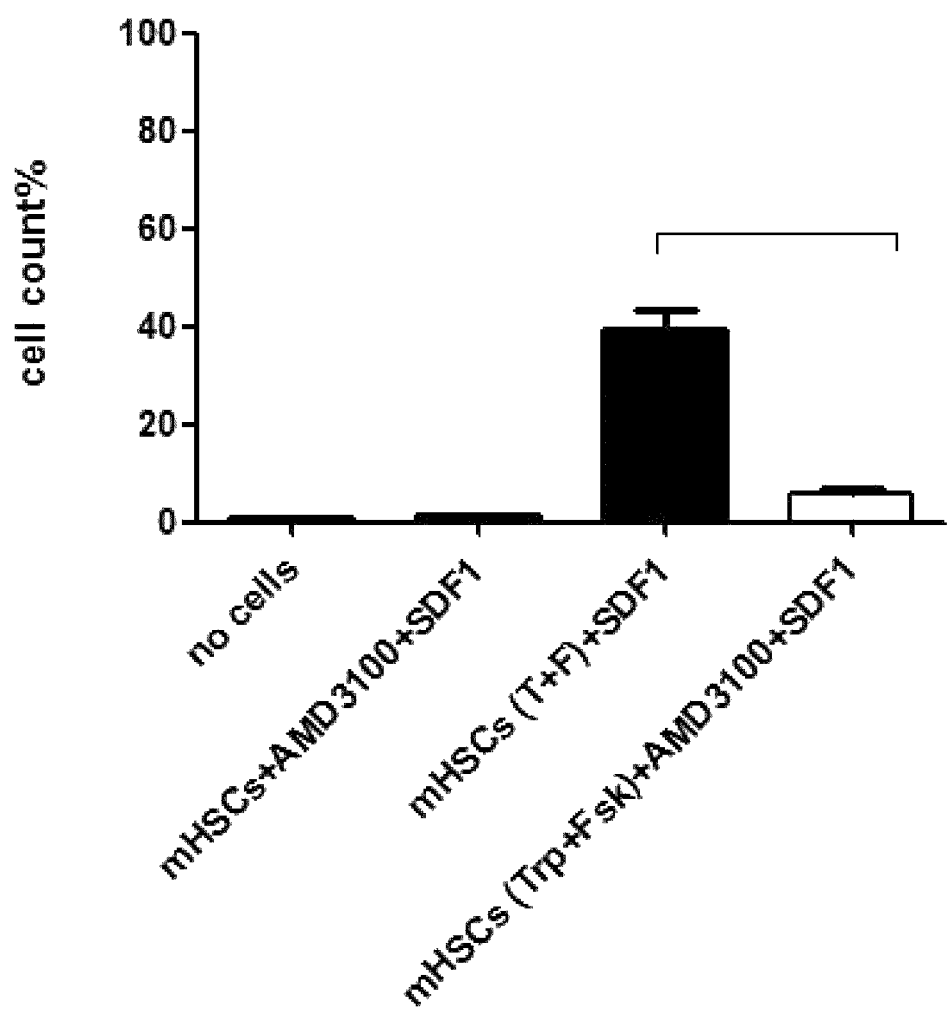

FIG. 2: Inhibition by the CXCR4 antagonist AMD3100 of the SDF-1/CXCL12-induced migration of murine haematopoietic stem and progenitor cells, which had been stimulated in the presence of Treprostinil and forskolin FIG. 3: Vildagliptin enhances the migration of haematopoietic stem and progenitor cells, which were preincubated with Treprostinil and forskolin, towards SDF-1/CXCL12

Figure 4:
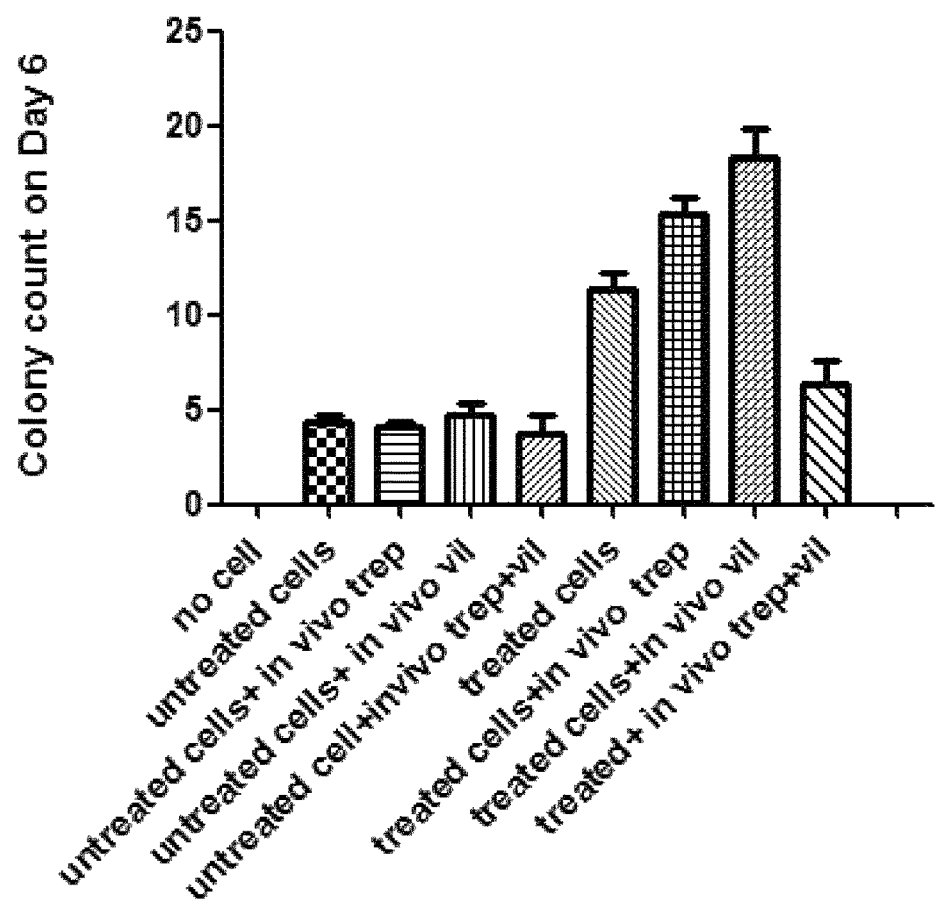

FIG. 4: Vildagliptin and Treprostinil increase homing of haematopoietic stem and progenitor cells, which were preincubated with Treprostinil and forskolin, but are mutually antagonistic when combined in vivo FIG. 5: The combined administration of Treprostinil and vildagliptin to lethally irradiated BALB/c recipient mice, which were injected with haematopoetic stem and progenitor cells pretreated in vitro with the combination of Treprostinil and forskolin, is less effective in enhancing survival of these mice than the sole in vivo administration of either vildagliptin or Treprostinil.

Figure 6:
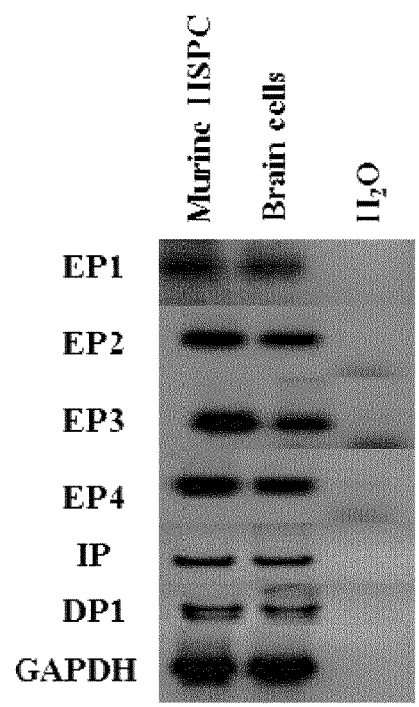
Figure 6:
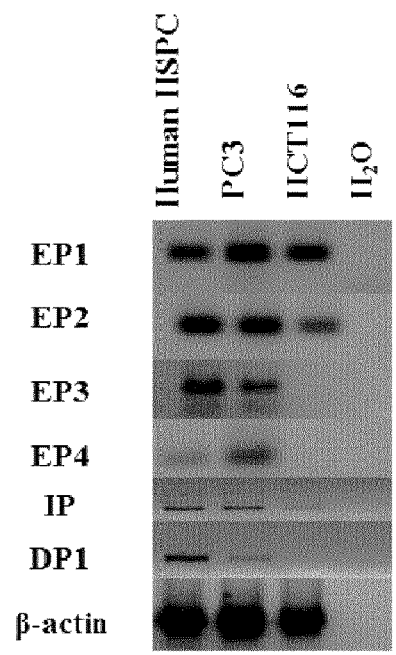

FIG. 6: Prostanoid receptor expression (A, B) in murine and human haematopoetic stem and progenitor cells (HSPCs). RNA was isolated from murine (A) and human HSPCs (B) and reverse transcribed. RNA prepared from murine brain cells (mixed culture of neurons and glial cells) and the human cell lines PC3 and HCT116, served as positive controls. PCR-dependent amplification was done using primers listed in Table 1. Amplicons for all E prostanoid receptors (EP1 to EP4), the I prostanoid receptor (IP) and the D prostanoid receptor-1 (DP1) were electrophoretically resolved on an agarose gel and visualized by ethidium bromide staining. The lane labelled H2O denotes the control, where the amplification was done in the absence of prior reverse transcription. The mRNA encoding GAPDH was amplified as internal reference.

Figure 7:
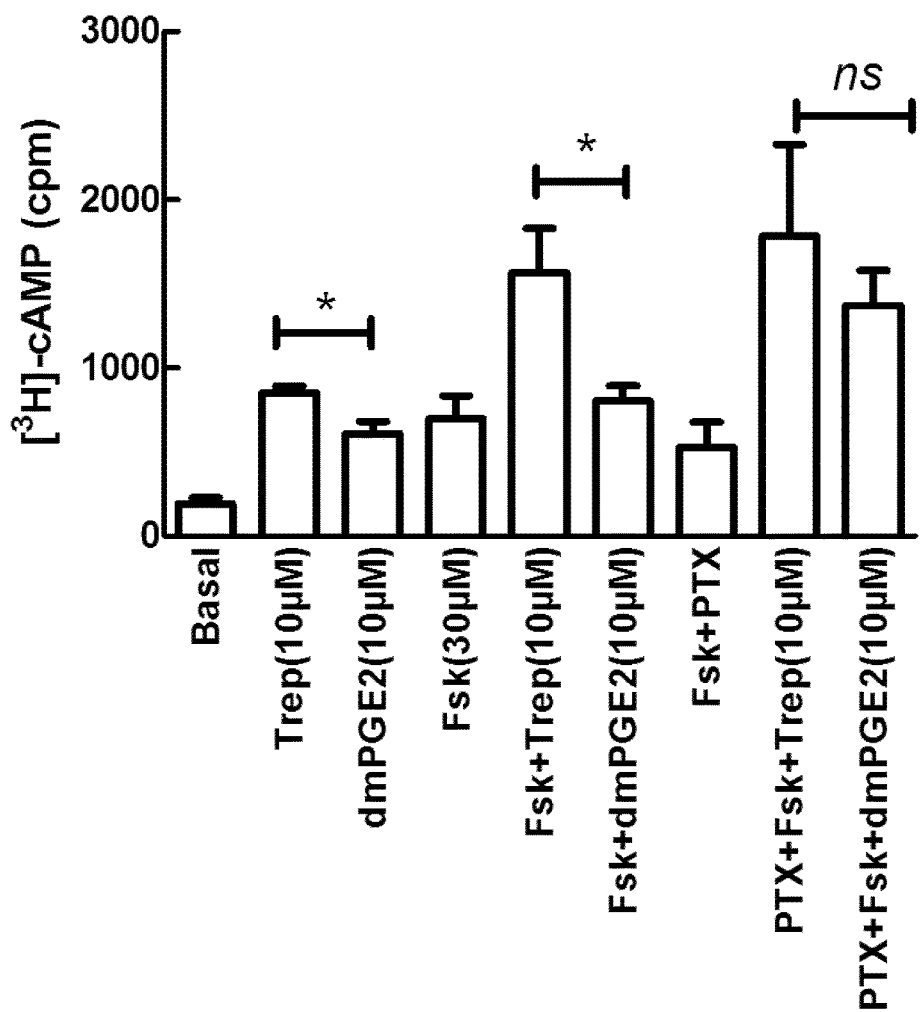

FIG. 7: Comparison of Treprostinil- and dmPGE2-induced cAMP accumulation in human HSPCs.

Figure 8:
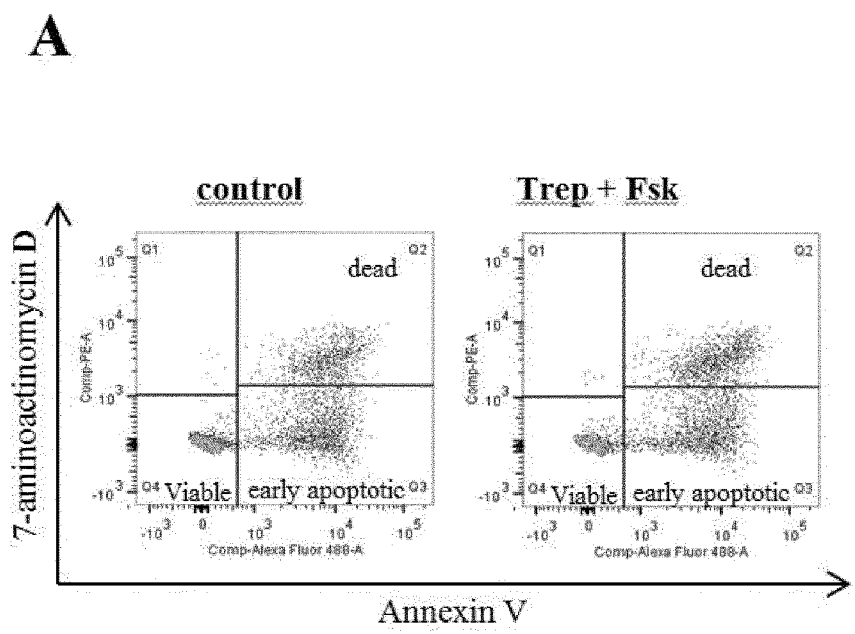
Figure 8:
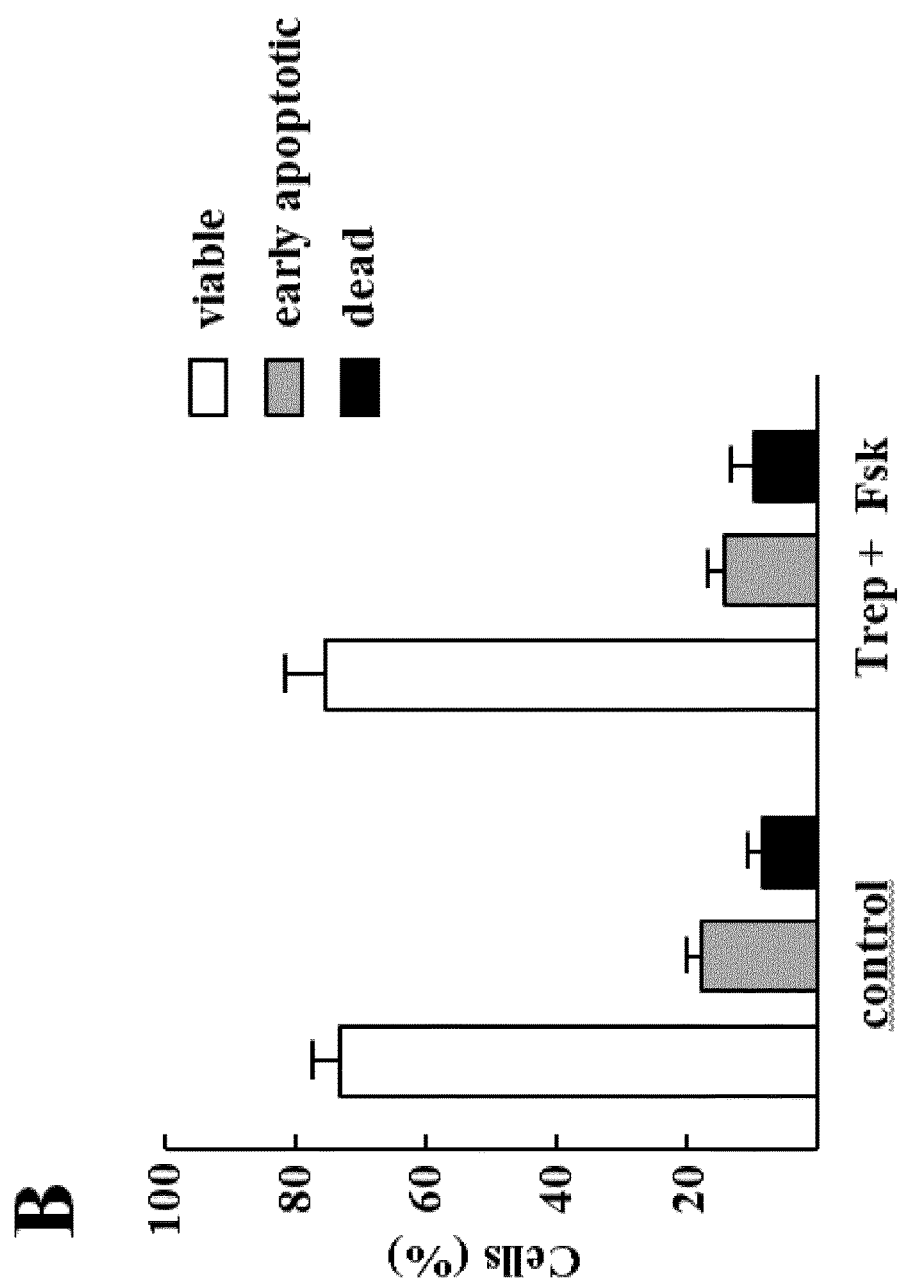
Figure 8:
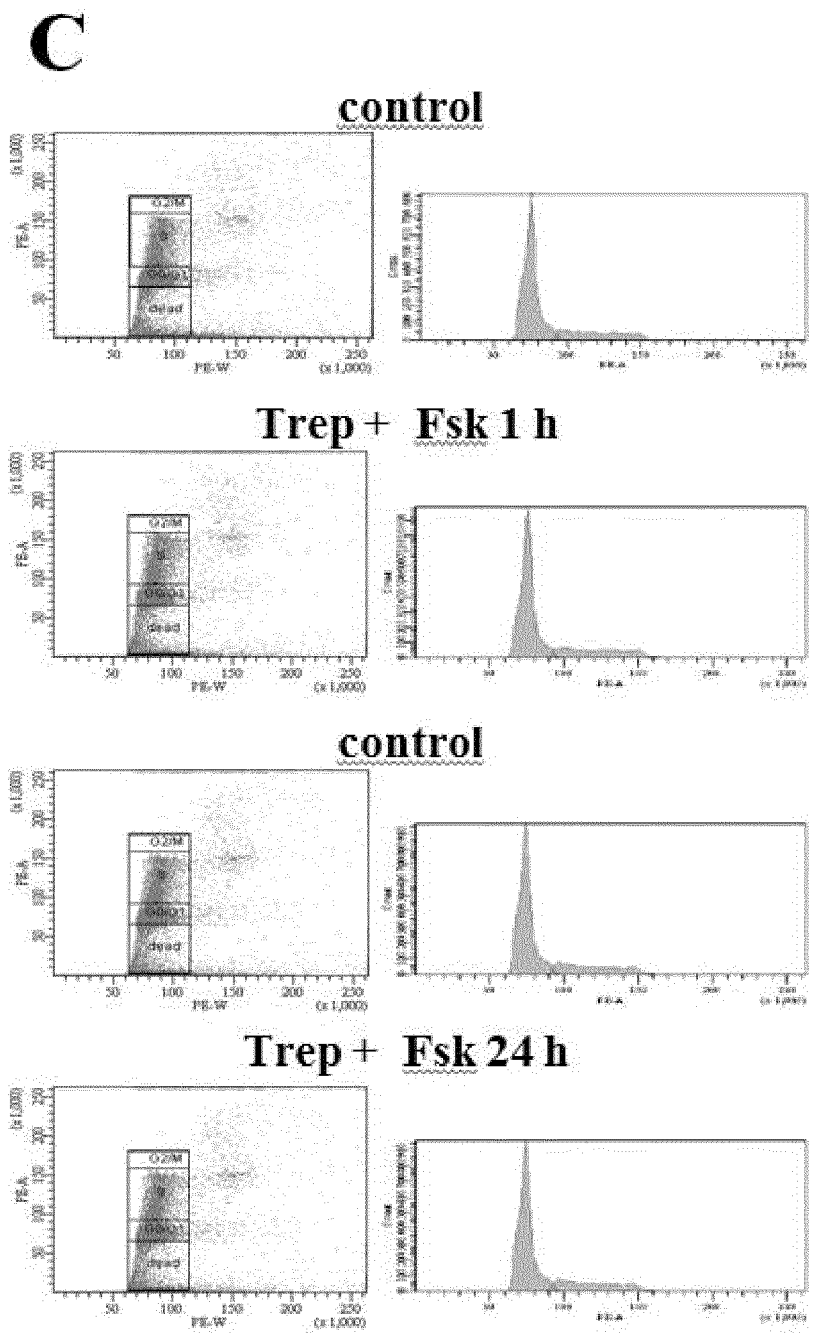
Figure 8:
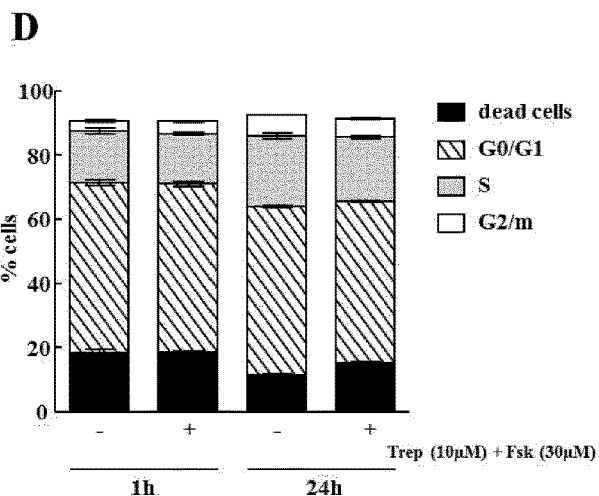
Figure 8:
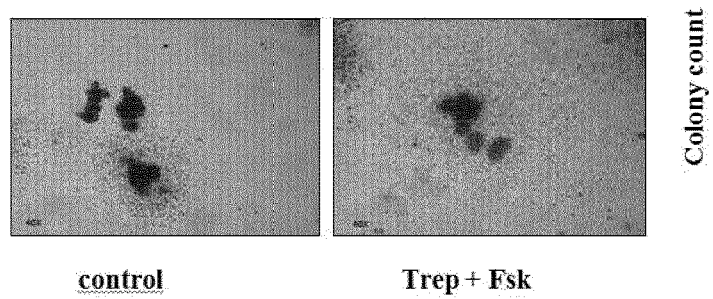
Figure 8:
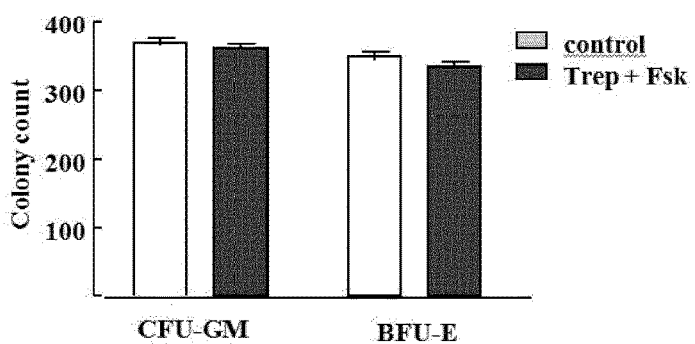

FIG. 8: Pretreatment of murine and human HSPCs with Treprostinil and forskolin does neither induce apoptosis nor alters cell cycle progression or differentiation potential. Human HSPCs were incubated with 10 μM Treprostinil and 30 μM forskolin for 1 h. Subsequently, (A, B) apoptosis induction and (C, D) cell cycle progression was assessed by flow cytometric analysis. No difference in apoptotic cells or distribution of cells according to G0/1, S and G2 phase was detected between untreated and treated cells (one way ANOVA). (E, F). Data are means±SEM (n=3).

Figure 9:
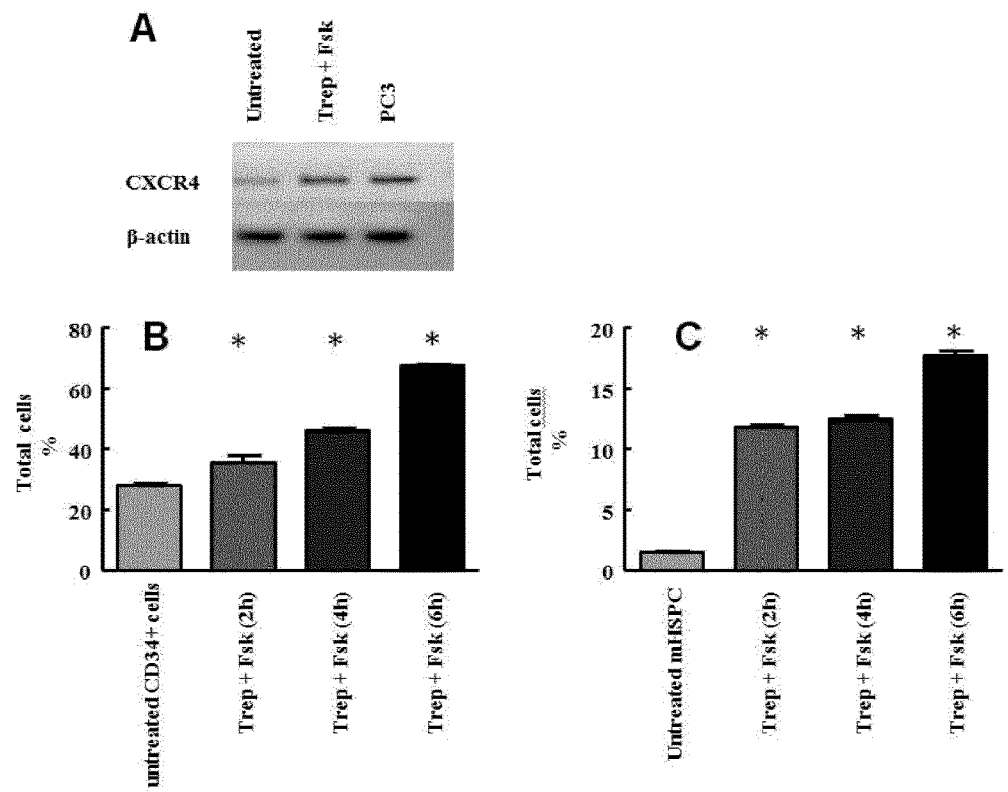

FIG. 9: In vitro pretreatment with Treprostinil and forskolin enhances expression of CXCR4 (A & B) and CD26/DPPIV (B).

Figure 10:
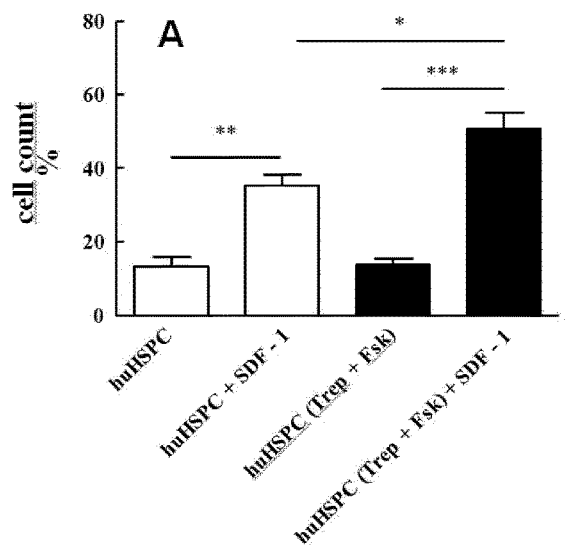
Figure 10:
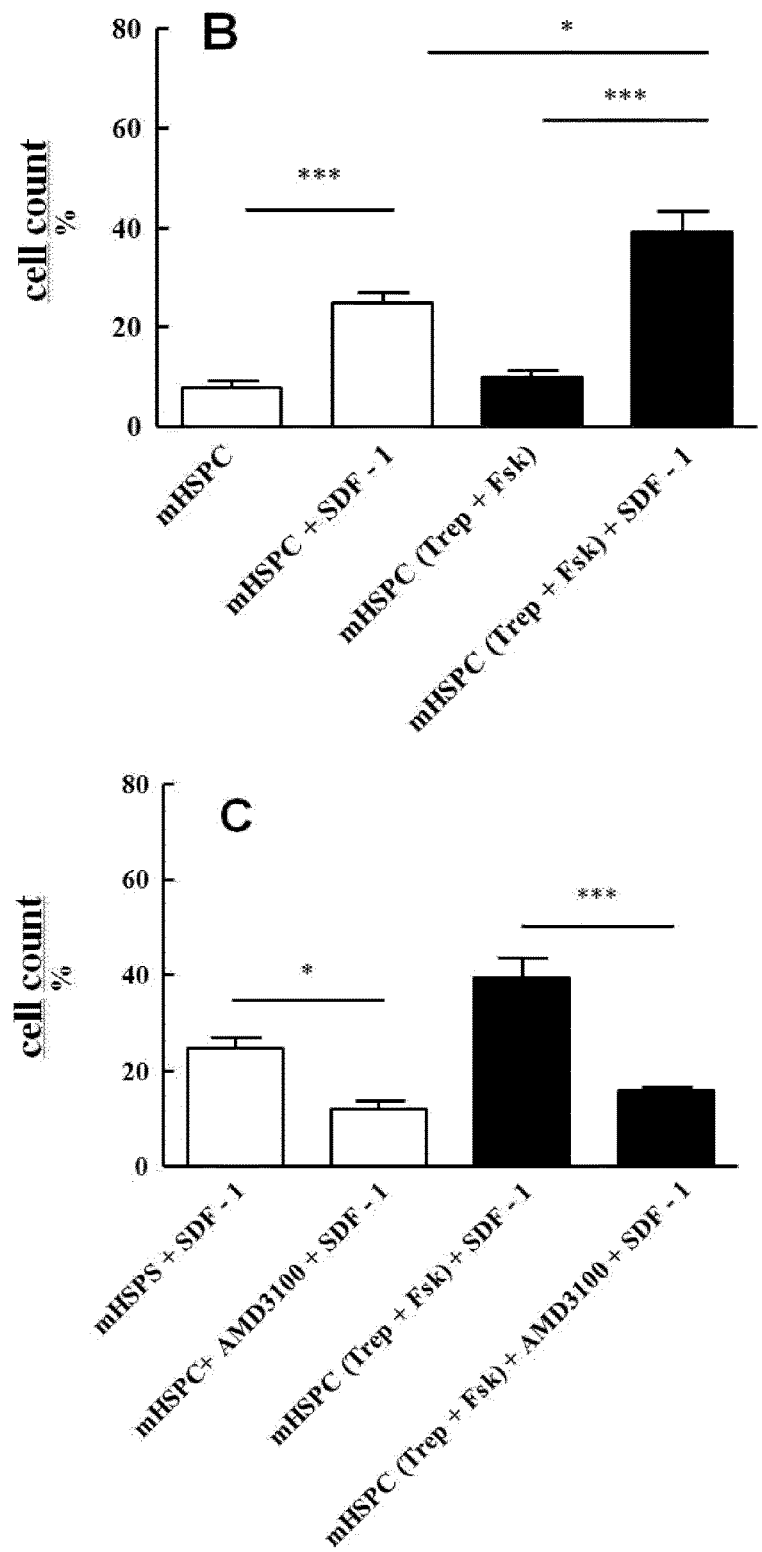

FIG. 10: In vitro pretreatment with Treprostinil and forskolin enhances the action of SDF-1 via CXCR4.

Figure 11:
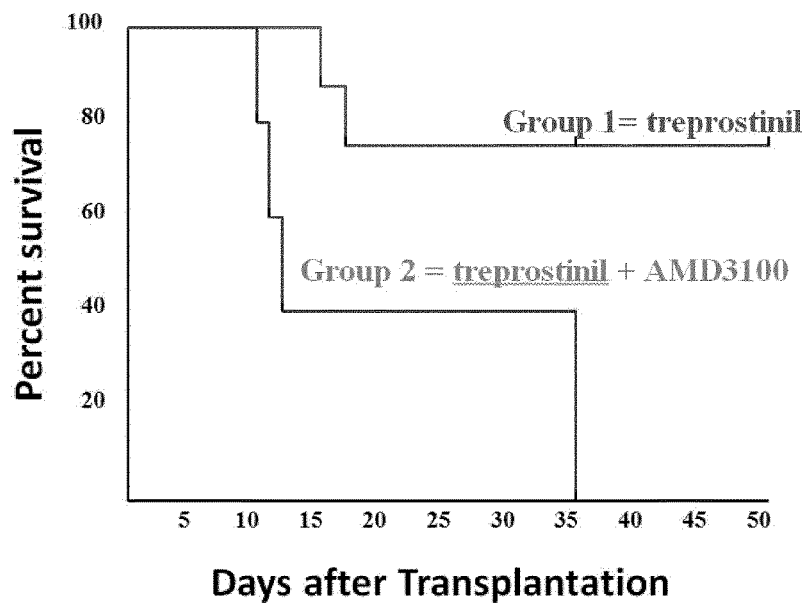

FIG. 11: In vivo administration of CXCR4-antagonist (AMD3100) abrogates the beneficial effect of Treprostinil on the survival of recipient mice. Murine HPSCs were pretreated in vitro with Treprostinil and forskolin as outlined in the legend to FIG. 4 and injected ($2\times10^5$ per mouse) into lethally irradiated recipient mice. These were subsequently divided in two groups. Mice allocated to group 1 (n=10) were further subjected to in vivo treatment with Treprostinil (0.15 mg $kg^{-1}$ 8 $h^{-1}$) whereas mice in group 2 (n=10) received both Treprostinil (0.15 mg $kg^{-1}$ 8 $h^{-1}$) and AMD3100 (3.3 mg $kg^{-1}$ 8 $h^{-1}$) by subcutaneous injection every 8 h for 10 days. The difference between the two survival curves was statistically significant (P=0.007, log-rank test).

Figure 12:
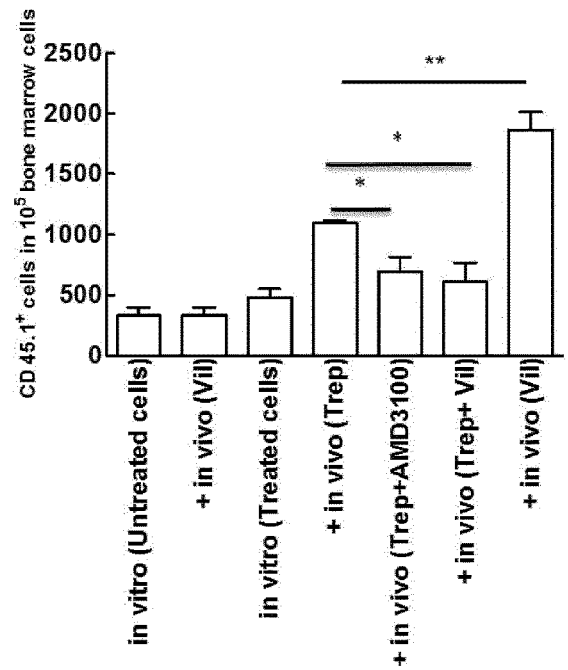

FIG. 12: In vivo treatment of recipient mice with sole vildagliptin and Treprostinil but not with their combination increases homing of HSPCs, which had been preincubated with Treprostinil and forskolin.

Figure 13:
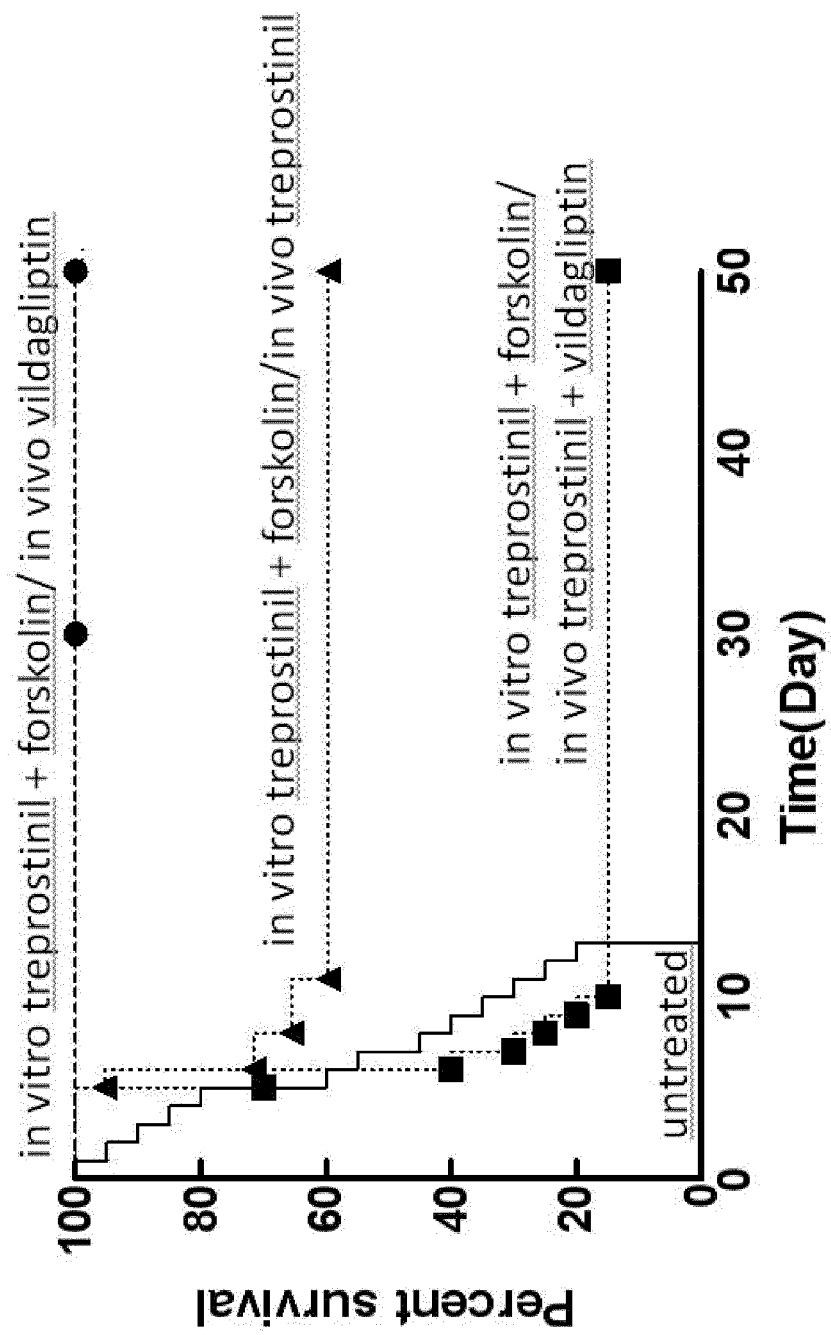

FIG. 13: Sole in vivo administration of the DPP-IV inhibitor vildagliptin increases the beneficial effect of in vitro treatment of HSPCs with Treprostinil and forskolin on survival rate in recipient mice.

DETAILED DESCRIPTION OF THE INVENTION

Providing methods and means to increase homing and engrafting of HSCs to the bone marrow environment has strong biologic and medical implications. The localization of stem cells following transplantation is highly important for clinical procedures as currently massive numbers of stem cells are required in clinical transplantation thus leading to the need of high amounts of donor cells. Such methods are also highly useful because a significant number of autologous donor transplants contain insufficient numbers of stem cells, or HSCs. Likewise, patients are often unable to find histocompatible donors, emphasizing the need for methods and compositions for reducing the number of HSCs needed for successful transplantation. The ability to improve homing and engrafting properties of HSCs in vitro or ex vivo allows the collection of fewer cells from donors, thereby reducing the time and discomfort associated with bone marrow/peripheral stem cell harvesting, and increasing the pool of willing HSC donors.

The present invention provides a novel use of dipeptidyl peptidase IV (DPP-IV) inhibitors in the treatment of patients who undergo transplantation of haematopoetic progenitor cells with the proviso that said stem cells used for transplantation had been incubated with at least one prostacyclin analogue for enhancing the engraftment of the cells, specifically with a cAMP enhancer before administration or returning said cells to an individual's body.

Haematopoetic stem and progenitor cells, specifically murine and human haematopoetic stem and progenitor cells (HSPCs) express several prostanoid receptors (i.e., $EP_1$, $EP_2$, $EP_3$, $EP_4$, IP and DP1, FIG. 6). Treprostinil is known to specifically activate all $G_s$-coupled receptors, i.e. $EP_2$, $EP_4$, IP and DP1 receptors whereas dmPGE2 also stimulates $EP_3$ receptors. The inventors have shown that Treprostinil stimulates cAMP in haematopoetic progenitor cells. In human haematopoetic stem and progenitor cells, the concentration-response curve for Treprostinil was more than two orders of magnitude between 10 and 90% of the response. This is consistent with the activation of several stimulatory receptors. Treprostinil-induced cAMP-accumulation can be enhanced upon combination with forskolin, a direct activator of adenylyl cyclase.

Haematopoetic stem and progenitor cells can be exposed to the combination of Treprostinil and forskolin without any detectable effect on their viability and their ability to subsequently undergo asymmetric cell division and differentiation into the erythroid and granulocyte/monocyte lineage. Thus the number of cells needed for transplantation is significantly less compared to the cells needed for transplantation without pre-treatment with a prostacyclin analogue and forskolin.

Pretreating haematopoetic stem and progenitor cells with the combination of Treprostinil and forskolin enhances bone marrow engraftment in irradiated organisms.

The additional treatment of recipient with Treprostinil in vivo further enhances bone marrow engraftment.

Said DPP-IV inhibitors are specifically selected from the group of gliptins.

As used herein and in the claims, the singular form, for example "a", "an" and "the" includes the plural, unless the context clearly dictates otherwise.

Specifically, the prostacyclin analogue is selected from the group of Treprostinil, Iloprost, Beraprost and Cicaprost or pharmaceutically acceptable salts thereof.

Treprostinil is a synthetic analogue of prostacyclin and is metabolically stable. Treprostinil is marketed as Remodulin™. Treprostinil is a (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid monosodium salt.

Iloprost is marketed as "Ilomedine" and is a 5-{(E)-(1S, 5S,6R,7R)-7-hydroxy-6[(E)-(3S, 4RS)-3-hydroxy-4-methyl-1-octen-6-inyl]-bi-cyclo[3.3.0]octan-3-ylidene}pentanoic acid.

Beraprost is a 2,3,3a,8b-tetrahydro-2-hydroxy-1-(3-hydroxy-4-methyl-1-octen-6-ynyl)-1H-cyclopenta(b)benzo-furan-5-butanoic acid.

Cicaprost is a 2-[(2E)-2-[(3aS,4S,5R,6aS)-5-hydroxy-4-[(3S,4S)-3-hydroxy-4-methylnona-1,6-diynyl]-3,3a,4,5,6, 6a-hexahydro-1H-pentalen-2-ylidene]ethoxy]acetic acid.

According to the present invention the term "prostacyclin analogues" includes functional derivatives and functional analogues of said substances.

The terms "analogue" or "derivative" relate to a chemical molecule that is similar to another chemical substance in structure and function, often differing structurally by a single element or group, which may differ by modification of more than one group (e.g., 2, 3, or 4 groups) if it retains the same function as the parental chemical. Such modifications are routine to skilled persons, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives can also include conjugates, such as biotin or avidin moieties, enzymes such as horseradish peroxidase and the like, and radio-labeled, bioluminescent, chemoluminescent, or fluorescent moieties. Further, moieties can be added to the agents described herein to alter their pharmacokinetic properties, such as to increase half-life ex vivo, or to increase their cell penetration properties, among other desirable properties. Also included are prodrugs, which are known to enhance numerous desirable qualities of pharmaceuticals (e.g., solubility, bioavailability, manufacturing, etc.).

The term "derivative" also includes within its scope alterations that have been made to a parent molecule including additions, deletions, and/or substitutions that provide for functionally equivalent or functionally improved molecules.

According to a specific embodiment of the invention, the Treprostinil derivative is selected from the group of acid derivatives of Treprostinil, prodrugs of Treprostinil, polymorphs of Treprostinil, anhydrous polymorphs of Treprostinil, or isomers of Treprostinil.

Similarly, Iloprost, Cicaprost or Beraprost can be derivatives from the group of acid derivatives, prodrugs, polymorphs or isomers therefrom.

According to a specific inventive embodiment, two, specifically three or more different prostacyclin analogues can be used in the inventive method. Alternatively, four, five or six or even more different prostacyclin analogues can be used.

Specifically, further to the prostacyclin analogue, (dimethylated) prostaglandin E2 may be used.

16,16-dimethyl $PGE_2$ is a competitive inhibitor of 15-hydroxy PGDH, but it is not a substrate for the enzyme. Because of its resistance to metabolism by 15-hydroxy PGDH, it has a prolonged half-life in vivo. 16,16-dimethyl $PGE_2$ acts as an agonist on most EP receptor subtypes. The $K_d$ for activation of isolated $EP_2$ receptors is about 1 nM.[3] 16,16-dimethyl $PGE_2$ is used to preserve the self-renewal properties while preventing the differentiation of hematopoietic stem cells during expansion in culture.[4,5]

DPP-IV is a non-classical serine, membrane-bound aminodipeptidase that removes Xaa-Pro dipeptides from the amino terminus of polypeptides and proteins. Within bone marrow, DPP-IV is localized in specialized microdomains on membranes of the connective tissue stroma.

Gliptins are a class of selective hypoglycemics that inhibit DPP-IV which are mainly used in the treatment of diabetes mellitus. Gliptins help lower the post-prandial glucose by inhibiting the breakdown of glucagon-like peptide 1 (GLP-1), an insulin secretagogue synthesized by gut wall cells in response to food.

Gliptins embodied in the present invention are specifically selected from the group consisting of sitagliptin, vildagliptin, alogliptin, saxagliptin, linagliptin, anagliptin, teneligliptin, gemigliptin or dutogliptin and any other gliptins which are shown to be potent inhibitors of purified, soluble or cell surface dipeptidylpeptidase.

Specifically, the administration of the DPP-IV inhibitor to the individual can be before, during or after administration of HSCs which had been pretreated according to the invention.

According to the invention, the terms "treating", "pretreating" or "incubation" can be used interchangeably. The terms are used with regard to isolated haematopoetic stem cells that are brought into contact with a prostacyclin analogue and a cAMP enhancer.

More specifically, it means that a sample containing haematopoetic stem cells is admixed with at least one prostacyclin analogue and at least one cAMP enhancer to obtain a mixture, incubating said mixture for a period of time sufficient to stimulate G alpha$_s$-signaling in said cells.

According to a specific embodiment, the composition for use may contain Treprostinil together with one of Iloprost, Beraprost or Cicaprost and a cAMP enhancer, specifically forskolin. Alternatively, Treprostinil can be admixed in combination with more than one, for example with two, three, four or five other prostacyclin analogues, for example, but not limited to Iloprost, Beraprost or Cicaprost or physiologically acceptable salts thereof in combination with a cAMP enhancer, specifically forskolin.

According to the inventive use, the DPP-IV inhibitor is vildagliptin and the haematopoetic stem cells had been treated in vitro with Treprostinil and forskolin before transplantation.

According to an alternative method, the DPP-IV inhibitor is selected from sitagliptin, alogliptin, saxagliptin and linagliptin, anagliptin, teneligliptin, gemigliptin and dutogliptin and the haematopoetic stem cells had been treated in vitro with Treprostinil and forskolin before transplantation.

According to a further alternative method the DPP-IV inhibitor is selected from sitagliptin, vildagliptin, alogliptin, saxagliptin and linagliptin, anagliptin, teneligliptin, gemigliptin and dutogliptin and the haematopoetic stem cells had been treated in vitro with Iloprost and forskolin before transplantation.

According to a further alternative method the DPP-IV inhibitor is selected from sitagliptin, vildagliptin, alogliptin, saxagliptin and linagliptin, anagliptin, teneligliptin, gemigliptin and dutogliptin and the haematopoetic stem cells had been treated in vitro with Beraprost and/or Cicaprost and forskolin before transplantation.

According to a specific embodiment the cyclic AMP (cAMP) enhancer or, as an alternative, a ligand to a prostaglandin EP receptor may be used for pretreatment of the stem cells. Examples of cAMP enhancers include, but are not limited to, dibutyryl cAMP (DBcAMP), phorbol ester, forskolin, sclareline, 8-bromo-cAMP, cholera toxin (CT), aminophylline, 2,4 dinitrophenol (DNP), norepinephrine, epinephrine, isoproterenol, isobutylmethyl-xanthine (IBMX), caffeine, theophylline (dimethylxanthine), dopamine, rolipram, prostaglandin $E_1$, prostaglandin $E_2$, pituitary adenylate cyclase activating polypeptide (PACAP), and vasoactive intestinal polypeptide (VIP), among others known in the art can be added to the stem cells or the stem cells/Treprostinil or stem cells/Treprostinil, Iloprost, Cicaprost and/or Beraprost mixture before incubation. Examples of cAMP enhancers also include cAMP and analogs of cAMP, such sp-5,6-DCI-BIMPS (BIMPS), among others.

Forskolin is specifically preferred to be comprised in the composition.

The amount of the prostacyclin analogue depends on the method for preparing stimulated HSCs.

Very specifically, for the inventive application, the effective concentration of Treprostinil is in the range of 0.1 µM to 100 µM, specifically 1 µM to 50 µM, specifically 5 µM to 25 µM, specifically about 10 µM.

According to the invention, the term "about" includes a deviation of the numerical value of a maximum of 10%, specifically a maximum of 5%, more specifically a maximum of 1%. As an example, the term "about 10 µM" thus defines a range of 9 to 11 µM, specifically 9.5 to 10.5 µM, specifically, 9.9 to 1.1 µM.

According to a further specific embodiment of the invention, the optimum concentration range for prostacylin analogue corresponds to 10 to 30 times of its $EC_{50}$ for stimulation of cAMP accumulation in said cells.

According to a specific embodiment of the invention, the ratio of prostacyclin analogue and forskolin may be about 1:3. The HSCs treated with forskolin and prostacyclin analogues may be purified before being reimplantated, however, these HSCs may also be re-implanted without further purification steps as low amounts of forskolin may be present but may not cause any negative side effects.

According to a specific aspect, the concentration of the cAMP enhancer, specifically of forskolin used for incubating the stem cells is may be between 1 μM and 100 μM, specifically between 10 μM and 50 μM about 30 μM.

The DPP-IV inhibitor is administered at least 5, specifically at least 10, specifically at least 15, specifically at least 24 hours before haematopoetic stem cell transplantation.

Alternatively, the DDP-IV inhibitor can be administered to the patient preoperatively, i.e. 1, 2, 3, 4, 5, 6, 7, 8, 9 or 10 days before undergoing transplantation and/or postoperatively, i.e. at least 5, specifically at least 10, specifically at least 15, specifically at least 24 hours after transplantation, up to 1, 2, 3, 4, 5, 6, 7, 8, 9, 10 or more days.

Specifically, vildagliptin can be administered to an individual in an amount of 50 to 200 mg/d, specifically 75 to 150 mg/d, specifically about 100 mg/d.

Specifically, sitagliptin can be administered to an individual in an amount of 50 to 200 mg/d, specifically 75 to 150 mg/d, specifically about 100 mg/d.

Specifically, saxagliptin can be administered to an individual in an amount of about 2.5 to 10 mg/d, specifically about 5 mg/d.

Specifically, linagliptin can be administered to an individual in an amount of about 2.5 to 10 mg/d, specifically about 5 mg/d.

Specifically, alogliptin can be administered to an individual in an amount of about 12.5 to 50 mg/d, specifically about 25 mg/d.

The inventive method advantageously provides stimulated stem cells, which can directly be administered to individuals and further stimulates homing and engraftment of said cells.

"Individual" is meant to broadly include any animal, specifically mammals, specifically humans who receive transplantation of stem cells pretreated according to the invention.

The HSCs treated with gliptin and prostacyclin analogue may be purified before being reimplanted, however, these HSCs may also be re-implanted without further purification steps.

The period of time which is needed to stimulate the G alpha$_s$-signaling in said cells can be measured according to known methods, for example by using cAMP measurements of which there are many variations: RIA, Fluorescence Resonance Energy Transfer (FRET) with EPAC (epac1) (Ponsiouen B. et al., EMBO reports, 5, 12, 1176-1180 (2004)), radiochemical methods etc. Stimulated cells wherein G alpha$_s$-signaling is occurring can be selected or discriminated or isolated from unstimulated cells by methods known in the art like a FRET-based cAMP reporter.

The period of time which is needed to inhibit CD26 peptidase activity and effective to increase migratory response to SDF-1 in said cells can be measured according to known methods, for example by fluorometric determination of the cleavage of Ala-Pro-7-amido-trifluoromethylcoumarin. Alternatively, the inhibition of the cleavage of natural substrates such as CXCL12 or GLP-1 can be monitored by HPLC or ELISA.

According to an embodiment of the invention, the incubation time for the respective cells is about 30 min to 24 h, preferably about 1 h and 12 h, preferably about 1 h to 4 h.

According to a further embodiment, the in vitro incubation time for the pretreatment of the HSCs with the prostacyclin analogue and the cAMP enhancer is at least 10 minutes, specifically at least 20 minutes, at least 30 minutes, at least 40 minutes, at least 50 minutes, at least 60 minutes.

According to a further aspect of the invention, at least $1 \times 10^5$ donor cells/ml are incubated with the prostacyclin analogue and the cAMP enhancer at about 37° C.

The cAMP-dependent pathway is an essential pathway for promoting engraftment of haematopoetic stem cells. It has been shown by the inventors that a prostacyclin analogue can trigger cAMP elevation in haematopoetic stem cells. It does so by activating multiple receptors, i.e. IP- and EP-receptors thus leading to increased G alpha$_s$-signaling. Accordingly, prostacyclin analogues like Treprostinil, Iloprost, Cicaprost or Beraprost are more effectively raising cAMP levels.

The term "haematopoetic stem cells" (HSCs) or the more general term "stem cells" are understood as equivalent terms in the description of the present invention, and generally relate to either pluripotent or multipotent "stem cells" that give rise to the blood cell types, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art.

"Stem cells" are usually characterized by their ability to form multiple cell types (i.e. being multipotent) and their ability for self-renewal. However, oligopotent and unipotent progenitors may be included also.

The term "progenitor cell" includes a biological cell that, like a stem cell, has a tendency to differentiate into a specific type of cell, but is already more specific than a stem cell and is pushed to differentiate into its "target" cell. Progenitor cells are early descendants of stem cells that can differentiate to form one or more kinds of cells. The most important difference between stem cells and progenitor cells is that stem cells can replicate indefinitely, whereas progenitor cells can divide only a limited number of times. Most progenitors are described as oligopotent, they may be compared to adult stem cells. Progenitors are said to be in a further stage of cell differentiation. They are in the "center" between stem cells and fully differentiated cells. The kind of potency they have depends on the type of their "parent" stem cell and also on their niche. Progenitor can move through the body and migrate towards the tissue where they are needed. Many properties are shared by adult stem cells and progenitor cells.

Progenitor cells are found in adult organisms and they act as a repair system for the body. They replenish special cells, but also maintain the blood, skin and intestinal tissues. They can also be found in developing embryonic pancreatic tissue.

"Haematopoesis" refers generally to the process of cellular differentiation or formation of specialized blood cells from an HSC. During development, haematopoesis translocates from the fetal liver to the bone marrow, which then remains the site of haematopoesis throughout adulthood. Once established in the bone marrow, HSCs are not distributed randomly throughout the bone cavity. Rather, HSCs are typically found in close proximity to the endosteal surfaces.

The more mature stem cells increase in number as the distance from the bone surface increases.

Haematopoetic tissues contain cells with long-term and short-term regeneration capacities, as well as committed multipotent, oligopotent, and unipotent progenitors.

The sample containing HSCs specifically can be bone marrow.

HSCs can be obtained by known techniques from any source known to contain HSCs, specifically from peripheral blood, umbilical cord or cord blood, placenta and bone marrow. Alternatively, also sources like fetal liver, fetal spleen, and aorta-gonad-mesonephros of animals are possible. HSCs from human origin are preferred for the methods and compositions of the invention.

For example, HSCs may be found in the bone marrow of adults, including femurs, hip, ribs, sternum, and other bones. HSCs may be obtained directly by removal from the hip using a needle and syringe, or from the blood, often following pre-treatment with cytokines, such as G-CSF (granulocyte colony-stimulating factors), that induce cells to be released from the bone marrow compartment.

HSCs may be identified according to certain phenotypic or genotypic markers. For example, HSCs may be identified by their small size, lack of lineage (lin) markers, low staining (side population) with vital dyes such as rhodamine 123 ($rho^{lo}$) or Hoechst 33342, and presence of various antigenic markers on their surface, many of which belong to the cluster of differentiation series (e.g., CD5, CD11b, CD34, CD38, CD90, CD133, CD105, CD45, GR-1 (=Ly-6G/C), 7-4, Ter-119 and c-kit). HSCs are mainly negative for the markers that are typically used to detect lineage commitment, and, thus, are often referred to as lin(−) cells. Most human HSCs may be characterized as $CD5^+$, $CD45R$ $(B220)^+$, $CD11^+$, $GR-1^+$, $CD34^+$, $CD59^+$, $Thy1/CD90^+$, $CD38^{lo/-}$, $C-kit/CD117^+$, and $lin(^-)$. However, not all stem cells are covered by these combinations, as certain HSCs are $CD347^+$ and $CD38^+$. Also some studies suggest that earliest stem cells may lack c-kit on the cell surface.

For purification of lin(−) HSCs by flow cytometry, or FACS, an array of mature blood-lineage marker antibodies may be used to deplete the lin(+) cells or late multipotent progenitors (MPP), including, for example, antibodies to CD3epsilon, CD5, CD45R, CD11b, CD16, GR-1, 7-4 and Ter-119, CD 13, CD32 and CD33, CD71, CD19, CD61, Mac-1 (CDI lb/CD18), Gr-I, 117Ra, CD3, CD4, CD5, and CD8 among others known in the art. Additional purification methods are known in the art, for example, methods that use the particular signature of the 'signaling lymphocyte activation molecules' (SLAM) family of cell surface molecules.

HSCs, whether from cord blood, bone marrow, peripheral blood, or other source, may be grown or expanded in any suitable, commercially available or custom defined medium, with or without serum. HSCs from human source are preferred embodiments of the invention. For instance, in certain embodiments, serum free medium may utilize albumin and/or transferrin. Further, cytokines may be included, such as Flt-3 ligand, stem cell factor (SCF), and thrombopoietin (TPO), among others. HSCs may also be grown in vessels such as bioreactors. A suitable medium for ex vivo expansion of HSCs may also comprise HSC supporting cells, such as stromal cells (e.g. lymphoreticular stromal cells), which can be derived, for instance, from the disaggregation of lymphoid tissue, and which have been show to support the in vitro, ex vivo, and in vivo maintenance, growth, and differentiation of HSCs, as well as their progeny.

"Cord blood" or "umbilical cord blood" relates generally to a relatively small amount of blood (up to about 180 ml) from a newborn baby that returns to the neonatal circulation. Cord blood is rich in HSCs and may be harvested and stored for later use according to techniques known in the art.

The terms "ex vivo" or "in vitro" refer to activities that take place outside an organism, such as experimentation or measurements done in or on living tissue in an artificial environment outside the organism, preferably with minimum alteration of the natural conditions. In certain embodiments, such tissues or cells can be collected and frozen, and later thawed for ex vivo treatment. Tissue culture experiments or procedures lasting longer than a few days using living cells or tissue are typically considered to be "in vitro" though this term can be used interchangeably with ex vivo. The recitations "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure to treat the stem or progenitor cells (e.g., an ex vivo administration step that involves incubating the cells with a composition of the present invention to enhance engrafting capabilities of HSCs), and then administered to the same or different individual after that optional treatment or procedure.

The amount of DPP-IV inhibitor administered to an individual depends on the characteristics of that subject, such as general health, age, sex, body weight, and tolerance to drugs, as well as the degree, severity, and type of reaction to Treprostinil and/or cell transplant.

The individuals who receive stem cell transplantation can suffer from any bone marrow disease, i.e. a disease wherein the normal bone marrow architecture is displaced by malignancies, sickle cell disease, myelodysplastic syndrome, myeloproliferative disorders, aplastic anaemia, or infections leading to a decrease in the production of blood cells and blood platelets. Said bone marrow disease can be for example leukemia, a defect of the blood cell compartment or a need for bone marrow transplantation after chemotherapy or irradiation treatment.

More specifically, the defect of the blood cell compartment can be a haemoglobinopathy like thalassaemia, defects in neutrophil granulocyte function, a defect in neutrophil granulocyte function, a defect in T- and/or B-lymphocytes, e.g., severe combined immunodeficiency, Bruton's agammaglobulinemia.

The use for the treatment of individuals suffering from bone marrow diseases, for example due to chemotherapy or irradiation and thus undergoing haematopoetic stem cell transplantation by administering a one or more DPP-IV inhibitors for a limited period of time after bone marrow transplantation is covered by the present invention.

At least one prostacyclin analogue together with one or more cAMP enhancers for pretreatment of isolated stem cells and administration of one or more DPP-IV inhibitors to the transplanted patients can be used for enhancing the engraftment of human HSCs during bone marrow transplantations or upon reconstitution of the bone marrow by using HSCs. Accelerated engraftment shortens the period at which subjects are susceptible to potentially lethal infections, bleeding and other serious complications. Hence, a prostacyclin analogue in combination with a gliptin ought to be a useful therapeutic option to pretreat donor bone marrow to enhance bone marrow engraftment (i.e., by reducing the number of cells required and shortening the duration of bone marrow aplasia).

Continuous treatment of subjects for several days after bone marrow transplantation with a DPP-IV inhibitor results in improved clinical outcome by improving engraftment (i.e., by reducing the number of cells required and shortening the duration of bone marrow aplasia).

Thus, according to a specific embodiment, the treatment is performed at least for one day, specifically five days after transplantation, more specifically for at least 10 days, more specifically for at least 14 days after transplantation.

The DPP-IV inhibitor can be administered to the subject by any mode applicable and known in the art. More specifically, enteral, intravenous or subcutaneous administration is provided.

Intravenous administration is the preferred mode of administration.

However, the DPP-IV inhibitor can be in an orally available form selected from the group of sustained release forms, tablets or capsules.

The invention also provides a kit of parts comprising
a) an amount of at least one prostacyclin analogue and forskolin in a first unit dosage form,
b) and an amount of at least one DPP-IV inhibitor selected from gliptin,
in the form of two, three, four or more separate units of components a) and b), specifically for use in the treatment of a bone marrow disease, specifically the bone marrow disease is leukemia, a defect of the blood cell compartment, bone marrow diseases induced by chemotherapy or irradiation.

The invention furthermore covers a package comprising the kit according to the invention together with instructions for use.

The foregoing description will be more fully understood with reference to the following examples. Such examples are, however, merely representative of methods of practicing one or more embodiments of the present invention and should not be read as limiting the scope of invention.

EXAMPLES

Example 1

In Vitro Migration Assay

Murine haematopoetic progenitor cells were pretreated in vitro with the combination of 10 µM Treprostinil (Trep) and 30 µM forskolin (Fsk) (Sigma Aldrich, Vienna, Austria) or vehicle for 1 h at 37° C. in growth factor containing stem cell medium [(StemSpan™ (SFEM) (Stemcell technologies, USA) (50 ng/mL murine stem cell factor (SCF), 50 ng/mL fms-like tyrosine kinase-3 ligand (Flt3), 50 ng/mL interleukin 11 (IL11) and 150 ng/mL murine interleukin 3 (mIL3)] purchased from PeproTech (London, United Kingdom)). Thereafter cells were washed and resuspended at $2 \times 10^6$ cells/mL in medium.

The cell suspension (0.1 mL containing $2 \times 10^5$ cells) was added to the upper chamber of Transwell™ dishes (5 µm pore diameter). The bottom chamber was followed with medium or medium containing 100 ng/ml murine stromal derived factor-1 (SDF-1=CXCL12). Cells were allowed to migrate for 4 h at 37° C. Subsequently, the number of cells recovered from the lower chamber was determined by a cell counter. The number of migrated cells was expressed as percentage of total cells added to the upper chamber.

Human umbilical cord blood derived CD34+ cells were maintained in stem cell medium [X-VIVO™ 15 (Lonza, Switzerland), supplemented with 50 ng/mL human Flt3, 50 ng/mL human thrombopoietin and 50 ng/mL human (SCF), purchased from PeproTech (London, United Kingdom)]. The migration assay was performed as described for murine cells, with the exception that recombinant human SDF-1 was added to the lower chamber. Data shown represent means±SEM from 3 independent experiments carried out in triplicate. Statistically significant differences were assessed by one-way ANOVA followed by Dunnett's multiple comparisons (*, p<0.05).

The data are shown in FIG. 1.

Example 2

Inhibition by the CXCR4 antagonist AMD3100 of the SDF-1/CXCL12-induced migration of murine haematopetic progenitor cells, which had been stimulated in the presence of Treprostinil and forskolin Hematopoietic stem and progenitor cells were preincubated with Treprostinil (10 µM; T) and forskolin (30 µM; F) for 1 h at 37° C., washed and resuspended at a cell density of $2 \times 10^6$ cells/mL. The cell suspension ($2 \times 10^5$ cells in 0.1 mL) was added to the upper chamber the Transwell™ dish, which contained medium with and without 10 ΞM CXCR4 antagonist AMD3100 (10 µM). The medium in the lower chamber contained 100 ng/ml murine SDF-1. The incubation lasted for 4 h at 37° C.; thereafter cells recovered in the lower chamber were counted as outlined in the legend to FIG. 1. Data shown are means±SEM from three independent experiments carried out in triplicate. Statistically significant differences were assessed by one way ANOVA followed by Dunnett's multiple comparisons (***, p<0.001).

The CXCR4 antagonist AMD3100 inhibits the SDF-1/CXCL12-induced migration of murine hematopietic progenitor cells, which were stimulated in the presence of Treprostinil and forskolin.

The data are shown in FIG. 2.

Example 3

Vildagliptin enhances the SDF-1/CXCL12-induced migration of hematopoietic progenitor cells, which had been preincubated with Treprostinil and forskolin.

Murine hematopoietic progenitor cells (mHPC; left hand panel) and human CD34+ cells derived from umbilical cord blood (right hand panel) were preincubated in the absence or presence of Treprostinil (10 µM; T) and forskolin (30 µM; F) for 1 h. Thereafter, the cell suspension ($2 \times 10^5$ cells in 0.1 mL) was added to the top chambers of the Transwell™ dishes, which contained medium with or without 30 nM vildagliptin (Vil). The medium in the lower chamber contained 100 ng/ml murine or human SDF-1 as appropriate. The incubation lasted for 4 h at 37° C.; thereafter cells recovered in the lower chamber were counted as outlined in the legend to FIG. 1. Data shown are means±SEM from three independent experiments carried out in triplicate. Statistically significant differences were assessed by one-way ANOVA followed by Dunnett's multiple comparisons (*, p<0.05; , p<0.01; *, p<0.001).

Figure 3:
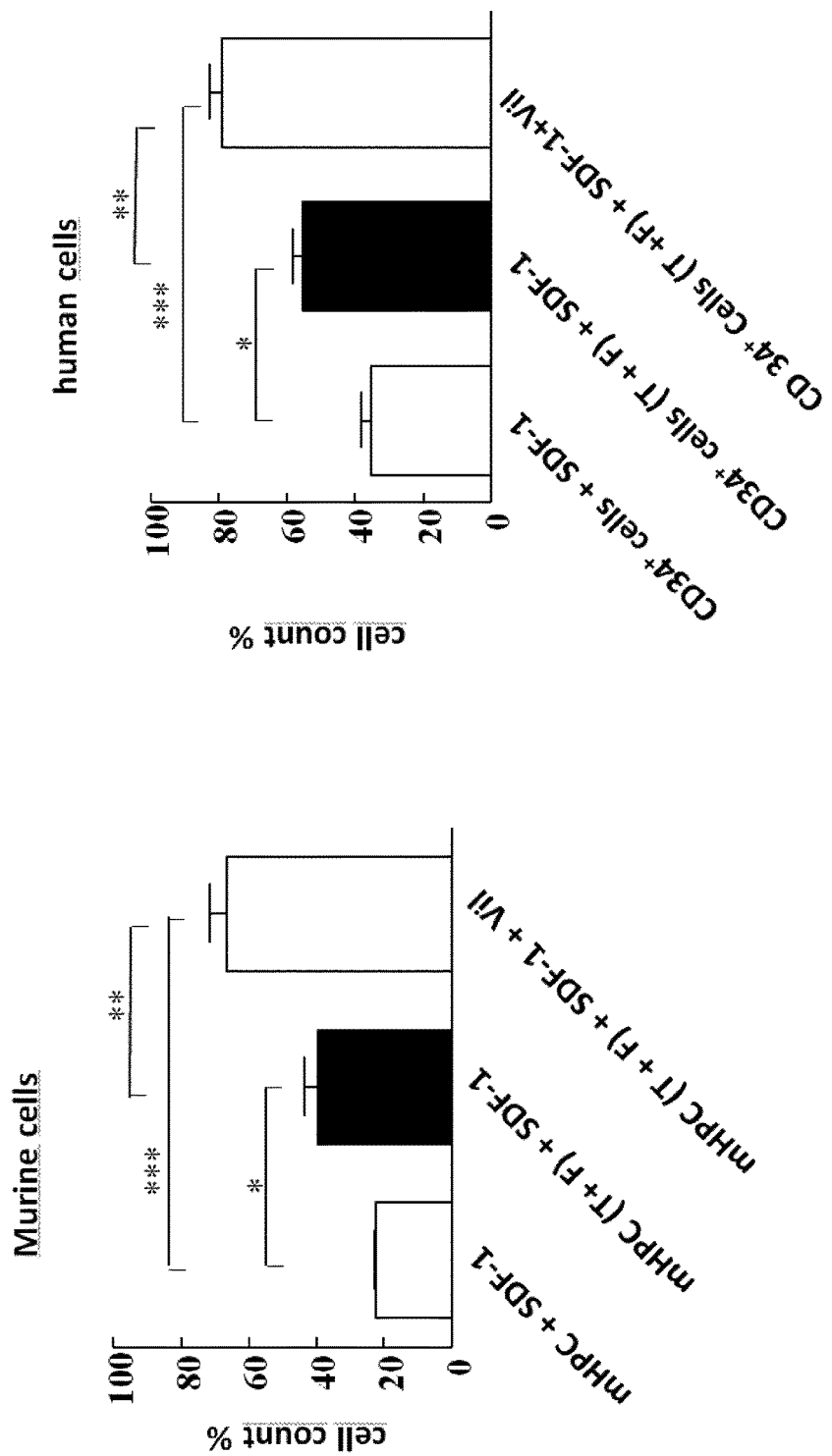

The data are shown in FIG. 3.

Example 4

In Vivo Homing Assay

Vildagliptin and Treprostinil increase homing of haematopoietic progenitor cells, which were preincubated with Treprostinil and forskolin, but are mutually antagonistic when combined in vivo.

Murine haematopoietic stem and progenitor cells were isolated from 6-8 week old BALB/c donor mice (15 mice) by magnetic cell sorting using lineage-specific antibodies which retained cells of the myeloid, erythroid, megakaryocyte and lymphoid lineage and MACS micro beads (Milteny Biotec, Bergisch Gladbach, Germany) according to the manufacturer's instructions. The sca1+, c-Kit+, lineage-negative (Lin−) cells were preincubated in the absence (vehicle control=untreated cells) and presence of the combination of Treprostinil (10 μM) and forskolin (30 μM) (=treated cells) for 1 h.

The (untreated and treated) haematopoetic stem progenitor cells ($1\times10^6$ cells) were subsequently injected via the tail vein into lethally (9 Gy) irradiated recipient BALB/c mice. Recipient mice did not receive any additional treatment (bars labeled untreated cells and treated cells) or the mice were injected with Treprostinil (3 μg/8 h; bars labeled "in vivo trep"), vildagliptin (10 mg/kg/24 h; bars labeled "in vivo vil") or the combination of Treprostinil and vildagliptin (bars labeled "in vivo trep+vil") starting 24 h prior to bone marrow transplantation.

The ability of cells to home into the bone marrow was assessed after 20 h by a colony formation assay. Femura and tibiae were flushed with PBS to collect bone marrow cells. Red blood cells were removed by red blood cell lysis buffer (Stemcell technologies, USA). The remaining cells were resuspended in a semisolid methylcellulose-based medium (MethoCult, stemcell technologies, USA). Each condition was assessed in triplicate. Specific growth factors were added to support the formation of both, colony-forming units, granulo-monocyte (CFU-GM) and colony-forming units erythrocyte (CFU-E), i.e., erythropoietin 3 U/mL, IL3 10 ng/mL, IL7 10 ng/mL, GM-CSF 10 ng/mL. The cultures were maintained for 6 days at 37° C. in a humidified atmosphere containing 5% $CO_2$. Thereafter, the number of colonies was counted under the microscope. By definition, these colonies arose from those cells, which had been injected and had migrated into the bone marrow, because the endogenous bone marrow of recipient mice had been destroyed by irradiation. Accordingly, no colonies were obtained, if bone marrow of irradiated mice, which had not been injected with haematopoetic progenitor cells, was plated (negative control).

It is evident that (i) the in vitro preincubation with Treprostinil and forskolin increased homing (cf. bars labeled untreated and treated), (ii) the sole treatment of the recipient mice with Treprostinil and/or vildagliptin did not promote homing (cf. second bar "untreated" with bars 3 to 5 labeled "+in vivo trep", "+in vivo vil", "+in vivo trep+vil"), (iii) the treatment of the recipient mice, which had been injected with treated cells, with either Treprostinil or vildagliptin promoted homing (cf. sixth bar "untreated" with bars 7 and 8 labeled "+in vivo trep", "+in vivo vil"), but (iv) that the combination (last right hand bar labeled "+in vivo trep+vil") was less effective than either compound administered alone (bars 7 and 8 labeled "+in vivo trep", "+in vivo vil"). Thus, when combined in vivo, Treprostinil and vildagliptin are mutually antagonistic.

Vildagliptin and Treprostinil increase homing of haematopoietic progenitor cells, which were preincubated with Treprostinil and forskolin, but are mutually antagonistic when combined in vivo. The data are shown in FIG. 4.

Example 5

In Vivo Engraftment Assay

The combined administration of Treprostinil and vildagliptin to lethally irradiated BALB/c recipient mice, which were injected with haematopoetic progenitor cells pretreated in vitro with the combination of Treprostinil and forskolin, is less effective in enhancing survival of these mice than the sole in vivo administration of either vildagilptin or Treprostinil.

Haematopoetic progenitor cells isolated from bone marrow of donor mice (BALB/c) as outlined in the legend to FIG. 4. The cells were treated in vitro with 10 μM Treprostinil and 30 μM forskolin or vehicle for 1 h at 37° C. After washing, $0.2\times10^6$ lineage-negative haematopoetic progenitor cells were injected via the tail vein into lethally irradiated (9 Gy) recipient BALB/c mice (10/group). If not pretreated in vitro with the combination of Treprostinil and forskolin, this number of haematopoetic progenitor cells is too low to rescue the recipient animals. Accordingly, the group of mice, which received cells that had not been pretreated, died within the first week (black line, CTRL). The limiting number of haematopoetic stem cells sufficed to rescue 50% of the mice, which had received pretreated cells and were then treated with Treprostinil (3 μg/8 h s.c. for 10 days; red curve labeled in vitro pretreated cells+in vivo treatment of recipient mice with Treprostinil). The most effective regimen was the injection of pretreated haematopoetic progenitor cells followed by the administration of vildagliptin (10 mg/24 h s.c.): all mice (i.e., 10 out of 10) survived (curve labeled in vitro pretreated cells+in vivo treatment of recipient mice with vildagliptin). In contrast, mice, which received the combination of Treprostinil (3 μg/8 h) and vildagliptin (10 mg/kg/24 h) had the worst outcome of all recipient mice that had received pretreated cells: only 2 out of ten mice survived (grey line labeled in vitro pretreated cells+in vivo treatment of recipient mice with the combination of Treprostinil and vildagliptin). Drug injections (i.e., administration of Treprostinil and/or vildagliptin by subcutaneous injections) were initiated immediately after haematopoetic progenitor cell transplantation and continued for 10 days. All curves are significantly different from each other (log rank test).

Figure 5:
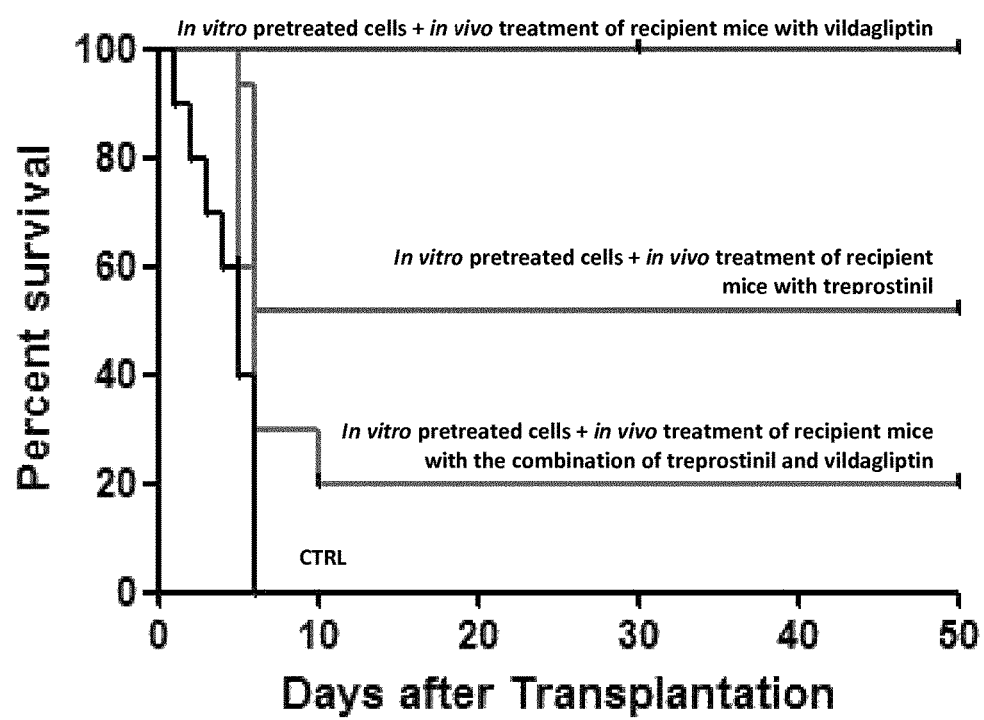

The combined administration of Treprostinil and vildagliptin to lethally irradiated BALB/c recipient mice, which were injected with haematopoetic progenitor cells pretreated in vitro with the combination of Treprostinil and forskolin, is less effective in enhancing survival of these mice than the sole in vivo administration of either vildagliptin or Treprostinil. The data are shown in FIG. 5.

Example 6

We explored the conditions, under which the action of Treprostinil and forskolin was further enhanced. This was based on the observation that the action of the combination of Treprostinil and forskolin was mediated at least in part by induction of the CXCR4-receptor (i.e., the receptor for the chemokine stromal-derived factor−1=SDF1=CXCL12). In addition, we compared the effect of dimethyl-PGE2 and Treprostinil on cAMP accumulation by human HSPCs.

Materials and Methods

Isolation of Murine and Human Haematopoetic Stem and Progenitor Cells

Ten mice (C57BL/6 or Balb/C) were sacrificed by cervical dislocation. The long bones of the hind limbs (i.e., femora and tibiae) were freed of muscle and connective tissue and flushed with RPMI medium using a syringe and 27½ G needle. The cell suspension was freed from visible connective tissue, collected and transferred to centrifuge tubes. Cells were harvested by centrifugation (1,200 rpm/~100 g for 5 min) and resuspended in 3 mL erythrocyte lysis buffer (0.15 M $NH_4Cl$, 10 mM $KHCO_3$, 0.1 mM EDTA, pH adjusted to 7.2 to 7.4). The cell suspension was incubated for 2 min at 20° C. followed by 4 min on ice. Thereafter, RPMI (10 mL) was added and the cells were harvested by centrifugation and counted. The typical yield of cells was $3*10^7$/mouse.

Cells were resuspended in ice-cold PBS (phosphate buffered saline) containing 2% FCS (fetal calf serum) at a cell density of $2.5*10^8$ cells/mL to which a cocktail of biotinylated antibodies ("Lineage Cell Depletion Kit" of Miltenyi Biotec) containing lineage-specific antibodies directed against CD5, CD45R (B220), CD11b, GR-1 (=Ly-6G/C), 7-4, and Ter-119 at a ratio of 0.1 mL antibody solution per $10^8$ cells. Cells were incubated for 20 min on ice with the antibodies and pelleted by centrifugation. After resuspension ($3.3*10^8$ cells/mL), the second anti-biotin-coated MicroBeads (0.2 mL/$10^8$ cells, provided with the ("Lineage Cell Depletion Kit" of Miltenyi Biotec) was added to the cell suspension and the mixture was incubated for 15 min on ice. Thereafter, the sample was diluted in MACS-buffer (30 mL), the cells were collected by centrifugation and resuspended in 6 mL of MACS-buffer. This suspension was loaded onto prepacked LS columns, which contain ferromagnetic beads coated with a cell-compatible plastic material. Typically three columns were employed for (2 mL cells suspension/column). The flow-through contained the lineage marker-negative cells ($Lin^-$ cells), while the lineage committed cells were retained on the column. Cells were pelleted by centrifugation and resuspended in 2 mL PBS. The typical yield was $7*10^5$ $lin^-$ cells/mouse.

Human haematopoetic stem and progenitor cells (HSPCs) were harvested from umbilical cords of healthy donors: cord blood samples ($\cong$50 mL) were collected during healthy full-term deliveries. CD34+ cells were isolated using magnetic-activated cell-sorter (MACS) Direct CD34 Progenitor Cell Isolation Kit (Miltenyi Biotech) and expanded as described (3). Briefly, cord blood was diluted with an equal volume of phosphate-buffered saline (PBS); this suspension (25 ml) was layered onto LymphoPrep™ (a density medium obtained through Nycomed which contains a mixture of sodium triatoate and polysaccharides). The tubes were centrifuged in a swinging bucket rotor for 30 min at 355 g. The layer containing mononuclear cells was harvested, diluted with PBS (to 50 mL) and centrifuged at 400 g for 8 min to remove residual LymphoPrep™. Erythrocytes were removed by lysis in buffer containing 150 mM $NH_4Cl$, 10 mM $KHCO_3$ and 0.1 mM EDTA (pH adjusted to 7.2 to 7.4 with HCl) for 10 min at 4° C. The number of mononuclear cells was determined and adjusted to $2*10^8$ cells/mL in the MACS buffer provided with the Isolation Kit. The EasySep® Positive Selection Cocktail was added (0.1 mL/mL cell suspension), the suspension was incubated for 15 min at room temperature and EasySep® Magnetic Nanoparticles (50 µL/mL) were added. After an additional incubation for 10 min at room temperature, the cell suspension was diluted to 2.5 mL by the addition of medium. The tube was placed into the magnet for 5 min and cells subsequently collected. This step was repeated 5 times. The enriched cells were propagated for 6 days (i.e., two population doublings) in suspension cultures containing serum-free X-VIVO15 medium (BioWhittaker) supplemented with GlutaMAX (2.5 mM; Gibco/Invitrogen) and penicillin/streptomycin (P/S; 125 U/mL each) and Flt3L, SCF and TPO (each at 50 ng/mL). Typical yields were $9*10^5$ CD34+ cells/cord blood specimen, which were expanded to obtain $3.5*10^6$ cells. All procedures were carried out in accordance with the guidelines from the Medical University of Vienna Institutional Review Board for these studies. Informed consent was provided in accordance with the Declaration of Helsinki Principles.

Flow Cytometry

The purity of murine and human haematopoetic stem and progenitor cell (HSPC) preparations was assessed by flow cytometry. The antibodies employed for staining of cell surface markers were from the following sources: the mouse lineage panel antibodies were from Becton Dickinson Biosciences (BD 559971, containing in biotinylated from anti-CD3ε, anti-CD11b, anti-CD45R, anti-Ly-6G/Ly-6c, anti-Ter-119), the affinity purified rat anti-mouse CD16/CD32 (mouse $Fc\gamma_{II/III}$ block, BD 553142) and the fluorescent dye streptavidin-allophycocyanin-Cy7 (streptavidin APC-Cy7, BD554063) were also from Becton Dickinson Biosciences. Phycoerythrin(PE)-Cy7-labelled anti-mouse Ly6A/E (=stem cell antigen–1=Sca1) PE-Cy7 (catalogue no. 25-5981-82) and PE-Cy5 anti-mouse CD117 (c-Kit) (catalogue no. 15-1171-81) were from eBiosciences.

Directly after MACS, $1*10^6$ lineage positive (Lin+) and negative (Lin−) cells were transferred into FACS (fluorescence-activated cell sorting) tubes and stored on ice in 50 µL PBS. In the meantime, the following antibodies suitable for FACS were diluted (1:50) and mixed in PBS: anti CD16/CD32 purified (to block Fc-receptors), biotinylated anti-CD3ε, biotinylated anti-CD11b, biotinylated anti-CD45R, biotinylated anti-Ly-6G/Ly-6C, and biotinylated anti-Ter-119, streptavidin-labelled APC-Cy7, PE-Cy7-labeled anti-Sca-1, PE-Cy5-labeled anti-c-kit. This master mix (50 µL) was added to each sample, which were then mixed by gentle vortexing and incubated at 4° C. in the dark for 15 min. Thereafter, the cells were harvested by centrifugation, washed in 2 mL PBS and resuspended in PBS. Samples were analysed in a FACS Canto II (Becton Dickinson). The gating procedure was as follows: the gates for live cells were set by recording forward and sideward scatter. Live cells were further discriminated based on the expression of lineage markers (i.e., CD11b, CD45R, Ly-6G/Ly-6C, Ter-119). This allowed for defining the gates for $Lin^-$ cells, which were further analysed for the expression of Sca-1 and c-Kit.

Flow cytometry was also used to monitor the expression of CXCR4 and CD26/DPPIV (dipeptidylpeptidase-IV) by human HSPCs. CXCR4 and CD26/DPPIV expression was measured after treatment with 10 µM Treprostinil and 30 µM forskolin for 2 h, 4 h and 6 h. After the incubation, human $CD34^+$ cells were washed and stained with antibodies (eBioscience) to CXCR4 and CD26 in accordance to the instructions of the manufacturer and quantified by FACS analysis. Three independent experiments were carried out separately and then the data were averaged for statistical analysis. Data are presented as mean±SEM, and comparisons were made using one-way ANOVA.

[$^3$H]cAMP Accumulation Assay

Human haematopoetic CD34+ stem and progenitor cells (HSPCs, $4*10^5$/mL) were first preincubated for 16 h in the absence presence of 100 ng/ml pertussis toxin (Sigma Aldrich) in X-VIVO15 medium supplemented with growth factors followed by metabolic labelling of the adenine nucleotide pool by an additional 4 h incubation period in [$^3$H]adenine (Perkin Elmer, 1 µCi/mL) in the X-VIVO15 medium supplemented with growth factors and 10 µg/mL adenosine deaminase (Roche). Thereafter, the cells were challenged with 1 or 10 µM Treprostinil, 1 or 10 µM dimethyl-PGE2 (dmPGE2), forskolin (30 µM) or the combination of forskolin and prostanoids for 30 min. The cells were then pelleted (5 min at 100 g), the medium was removed and the pellet was lysed in ice-cold 2.5% perchloric acid (0.9 mL) containing 0.1 mM cAMP, held on ice for 1 h and neutralized with 4.2 M KOH (0.1 mL). ATP and cAMP were separated by sequential chromatography on columns containing Dowex AG50-X8 and neutral alumina (3).

Cell Viability, Cell Cycle Distribution and Colony Formation

Human or murine HSPCs were incubated in the presence of vehicle or the combination of 10 μM Treprostinil and 30 μM forskolin at 37° C. for 1 h and 24 h. After washing with PBS at 4° C., cells were stained for externalized phophatidylserine with the PE Annexin-V Apoptosis Detection Kit I® according to the manufacturer's protocol or for DNA content with PI (50 μg mL−1 in PBS) for 40 min at 37° C. Data obtained by flow cytometry were analyzed with Facs Diva Software®. Colony formation of murine HSPCs was determined as follows: after an incubation for 1 h in the presence of 10 μM Treprostinil and 30 μM forskolin, cells were resuspended in MethoCult® containing GM-CSF and IL-3 (10 ng mL−1 each) for the formation of CFU-GM and 3 U mL−1 EPO and IL-3 for CFU-E, and cultured at 37° C. and 5% CO2 for 7-10 days. The number of colonies was counted under a light microscope.

Migration Assay

Murine lineage-negative haematopoetic stem and progenitor cells (HSPCs) from bone marrow of BALB/c donor mice and human CD34+ HSPCs isolated from umbilical cord blood were stimulated with the combination of 10 μM Treprostinil and 30 μM forskolin for 1 h either in the murine stem cell medium (SFEM™; 50 ng mL−1 of each growth factors; SCF, Flt3, IL11 and 150 ng mL−1 IL3) or human stem cell medium (X-VIVO™ 15, 50 ng mL−1 of each TPO, FL3, and SCF). After washing, the cell suspension ($2 \times 10^6$ cells in 0.1 mL) was placed in the upper chamber of a Transwell™ (6.5 mm diameter, 3-μm pore-size). The lower chamber was filled with 300 μL medium containing growth factors and 100 ng ml−1 SDF-1. Where indicated, both, the upper and bottom chamber were supplemented with 30 nM vildagliptin. Chemotaxis to SDF-1 was determined after 4 h incubation at 37° C. HSPCs, which had migrated to the bottom chamber, were counted in a cell counter. Assays were done in triplicate.

Homing Assay

The lineage-negative HSPCs were isolated from whole bone marrow cells of donor mice B6.SJL-PtrcAPep3B/Boyl (CD45.1+) using MACS micro beads (see above). The cells were in vitro treated with 10 μM Treprostinil and 30 μM forskolin or vehicle control for 1 h at 37° C. After washing, $0.2 \times 10^6$ lineage-negative CD 45.1+ cells were injected in to the lethally irradiated (10 Gy) recipient C57Bl/6 (CD45.2+) mice. Recipient mice were also treated in vivo with either Treprostinil (0.15 mg kg 8 h−1), vildagliptin (10 mg kg−1) or with the combination of both drugs subcutaneously. Control mice were injected with the same volume of vehicle. The whole bone marrow cells were isolated from recipient mice 16 h after transplantation. After lysis of red blood cells, the cells were stained for CD45.1 and CD45.2 markers. The proportion of CD45.1+ and CD45.2+ cells in the bone marrow was determined by flow cytometry.

Bone Marrow Transplantation:

Isogenic recipient mice (C57BL/6 or BALB/c) were subjected to lethal irradiation. If not rescued by intravenous administration of haematopoetic stem and progenitor cells (HSPCs), these mice died within the first two weeks. Lin− (Sca1+ and c-Kit+) HSPCs cells were prepared as outlined above and were pretreated ex vivo in the absence and presence of the combination of 10 μM Treprostinil+30 μM forskolin (FSK) for 1 h at 37° C. Thereafter, the cells ($1\text{-}5 \times 10^5$/mouse) were injected via the tail vein. White blood cell counts were determined by FACS, blood samples were collected every 3 to 5 days starting on day 9 (where blood cell count was ~1 G/L. In some instances, mice (25-30 g) were also treated with (i) Treprostinil (0.15 mg kg 8 h−1) and vildagliptin (10 mg kg−1 12 h−1) or with the combination of both administered subcutaneously every 8 h for 10 days.

Isolation of RNA from Haematopoetic Stem and Progenitor Cells and Polymerase Chain Reaction:

RNA was isolated from murine human haematopoetic stem and progenitor cells ($3 \times 10^6$ cells), from mixed (i.e., neuronal and glial) cultures prepared from murine cerebral cortex, from the human prostate cancer cell line PC3 and the human colon carcinoma cell line HCT116 (as positive controls) using of 2 mL Trizol® (Invitrogen). The homogenized samples were incubated for 5 min at room temperature to permit the complete dissociation of nucleoprotein complexes. Chloroform (0.4 mL) was added to the cell lysate and the tube was shaken vigorously by hand for 15 seconds. After incubation for 3 min at room temperature, the sample was centrifuged at 12,000 g for 15 min at 4° C. Following centrifugation, the mixture separates into a lower red, phenol-chloroform phase, an interphase, and a colourless upper aqueous phase. The aqueous phase (RNA) was transferred into a fresh tube and the RNA precipitated by mixing with 1 ml isopropyl alcohol. After incubation at room temperature for 10 min, the sample was centrifuged at 12,000 g for 10 min at 4° C. The supernatant was removed and the gel-like RNA-pellet washed once with 2 ml of 75% ethanol. The sample was mixed by vortexing and centrifuged at 7,500 g for 5 min at 4° C. The RNA-pellet was air-dried for 10 min and dissolved in 80 μL (highly purified) water by passing the solution a few times through a pipette tip, and incubating for 10 min at 55° C. (stored at −20° C.).

RNA (1 μg) was reversed transcribed to cDNA with the RevertAid™ H Minus First Strand cDNA Synthesis Kit (Fermentas) in the presence of 1 μL oligo (dT) 18 primer, 4 μl 5× Reaction Buffer, 1 μl RiboLock™ RNase Inhibitor (20 u/μl), 2 μl 10 mM dNTP Mix, 1 μl RevertAid™ H Minus M-MuLV Reverse Transcriptase (200 u/μl) and purified water to give a total volume of 12 μl for 60 min at 42° C. followed by an incubation for 5 min at 70° C.

The amplification by polymerase chain reaction (PCR) of fragments of the human prostaglandin receptors and of CXCR4 was done with 1 μl cDNA, 1 μl 10 mM dNTPs, 1 μl forward primer [10 μM], 1 μl reverse primer [10 μM], 4 μl GoTaq® Buffer [5×], 0.2 μl GoTaq® Polymerase and purified water to a final volume of 20 μl (11.8 μl). The mixture was first incubated at 95° C. for 5 min followed by 40 cycles (45 s denaturation at 95° C., 30 s annealing at 57° C., 45 s extension at 72° C.) and a final extension for 5 min at 72° C. PCR products were separated on 2% agarose gels.

TABLE 1

Primers used (forward & reverse):

| | | | |
|---|---|---|---|
| HEP1F | GAGAGCCAGGGCGCAGT | MEP4F | TCTCTGGTGGTGCTCATCTG |
| | (SEQ ID NO 1) | | (SEQ ID NO 15) |

TABLE 1-continued

Primers used (forward & reverse):

| | | | |
|---|---|---|---|
| HEP1R | GCAAGGGCTCATGTCAGG (SEQ ID NO 2) | MEP4R | TGCAAATCTGGGTTTCTGCT (SEQ ID NO 16) |
| MEP1F | AGCAGGAGCCAAGTTCCAG (SEQ ID NO 3) | HCXCR4F | AGGAAGCTGTTGGCTGAAAA (SEQ ID NO 17) |
| MEP1R | CATCCGCTAGGCTCAGGTTA (SEQ ID NO 4) | HCXCR4R | CTCACTGACGTTGGCAAAGA (SEQ ID NO 18) |
| HEP2F | CCACCTCATTCTCCTGGCTA (SEQ ID NO 5) | CXCR4F | AGGTGCAGGTAGCAGTGACC (SEQ ID NO 19) |
| HEP2R | TTTCCTTTCGGGAAGAGGTT (SEQ ID NO 6) | CXCR4R | ACTCACACTGATCGGTTCCA (SEQ ID NO 20) |
| MEP2F | TTATGACCATCACCTTCGCC (SEQ ID NO 7) | MPIF | GGGCACGAGAGGATGAAGT (SEQ ID NO 21) |
| MEP2R | TAAAAACCGAAGAGCTCGGA (SEQ ID NO 8) | MPIR | GATGGCCTGAGTGAAGCCT (SEQ ID NO 22) |
| HEP3F | AGCGACCATTTGGAAAGATG (SEQ ID NO 9) | HPIF | GTGTGCTCCCTGCCTCTC (SEQ ID NO 23) |
| HEP3R | TGATGTGATCCTGGCAGAAA (SEQ ID NO 10) | HPIR | GGGGTTGAAGGCGTAGAAG (SEQ ID NO 24) |
| MEP3F | TGGATCCCTGGGTTTATCTG (SEQ ID NO 11) | MPGRDF | AAGGCTCCATAGTACGCACG (SEQ ID NO 25) |
| MEP3R | GGGAAACAGGTACTGCAATGA (SEQ ID NO 12) | MPGRDR | CTCAGACTACAGGCACGGGT (SEQ ID NO 26) |
| HEP4F | TTACTCATTGCCACCTCCCT (SEQ ID NO 13) | HPGRDF | CGGAGGTCTTCTGCTTCTTC (SEQ ID NO 27) |
| HEP4R | CGCTCCAAACTTGGCTGATA (SEQ ID NO 14) | HPGRDR | CACTATGTGTTCTCTGCCCG (SEQ ID NO 28) |

Results:

Treprostinil- and DmPGE2-Induced Cyclic AMP Accumulation Human Haematopoetic Stem and Progenitor Cells After metabolic labelling with [3H]adenine, human HSPCs were stimulated with Treprostinil (Trep, 10 μM), dmPGE2 (10 μM) or forskolin (Fsk, 30 μM), the combination of Treprostinil (10 μM) or of dmPGE2 (10 μM) with forskolin (30 μM) as outlined under Materials and Methods. Where indicated HSPCs had been pretreated with pertussis toxin (PTX) for 16 h prior to stimulation. Data are from three independent experiments carried out in triplicate, error bars indicate s.e.m. In the presence of 30 μM forskolin, 10 μM Treprostinil was more efficacious than 10 μM dmPGE2 (P=0.03; Wilcoxon test). This difference was abolished by pertussis toxin pretreatment (ns, not significant). The data are shown in FIG. 7.

The adenine nucleotide pool of human CD34+ haematopoetic stem and progenitor cells (HSPCs) was metabolically labelled with [$^3$H]adenine and their response to Treprostinil and to dimethyl-PGE2 (dmPGE2) was examined in the presence and absence of 30 μM forskolin. It is evident from FIG. 7 that Treprostinil was significantly more efficacious than dmPGE2, regardless of whether the cells were stimulated in the absence or presence of forskolin. This diterpene binds in the pseudosubstrate cleft between the catalytic C1 and C2 domains of adenylyl cyclase and renders the various isoforms of the enzyme more responsive to the stimulatory G protein $G\alpha_s$ (5-7). The lower efficacy of dmPGE2 can be rationalized by taking into account that dmPGE2 is also a full agonist at the $G_i$-coupled EP3 receptor (8,9) and thus causes both, a $G_s$-dependent stimulation of adenylyl cyclase via EP2 and EP4 receptors and a concomitant inhibition via $G_i$-coupled EP3-receptors. Pertussis toxin abolishes the interaction of Gi-coupled receptors with $G_i$ (and related G proteins such as $G_o$ and $G_t$) by ADP-ribosylating a cysteine residue four amino acids removed from the C-terminus of the $G\alpha_i$-subunit. Accordingly, HSPCs were preincubated for 16 h in the presence of pertussis toxin. This pretreatment increased the response to dmPGE2 (cf. 6$^{th}$ and 9$^{th}$ bar in FIG. 7) such that there was no significant difference between the cAMP response elicited by Treprostinil+forskolin and that caused by dmPGE2+forskolin (cf. 8$^{th}$ and 9$^{th}$ bar in FIG. 7). This confirms that there is a major difference in the action of dmPGE2 and of Treprostinil on human HSPCs: dmPGE2 engages a $G_i$-coupled receptor but Treprostinil does not.

Pretreatment of HSPCs with Treprostinil and Forskolin Does Not Alter Cell Viability, Cell Cycle Progression or Differentiation Potential A persistent elevation in cAMP may trigger apoptosis in hematopoietic cells (10). Enhanced engraftment of dmPGE2-treated HSCs was attributed to effects on cell survival, proliferation and homing (11). Treprostinil and dmPGE2 differ in their ability to recruit G proteins: dmPE2-induced recruitment of $G_i$ may be of particular relevance, because signalling via $G_i$ can lead to activation of the lipid kinase PI3-kinase and the downstream kinase AKT, which stimulates proliferation and survival of cells (12,13). We thus examined whether in vitro treatment of human HSPCs with the combination of 30 μM forskolin and 10 μM Pretreatment of murine and human HSPCs with Treprostinil and forskolin does neither induce apoptosis nor alters cell cycle progression or differentiation potential. Human HSPCs were incubated with 10 μM Treprostinil and 30 μM forskolin for 1 h. Subsequently, (A, B) apoptosis induction and (C, D) cell cycle progression was assessed by flow cytometric analysis. Representative original pictures are depicted (A, C, left hand panel) and data obtained in three independent experiments was summarized (B, D, right hand panel). No difference in apoptotic cells or distribution of cells according to G0/1, S and G2 phase was detected between untreated and treated cells (one way ANOVA). (E, F). Murine HSPCs were isolated from bone marrow, pretreated and resuspended in a methylcellulose medium containing growth factors required for supporting the differentiation and growth of colony-forming units of the granulomonocyte (CFU-GM) and of the erythrocyte lineage (BFU-E). After 10 days the number of colonies was counted under a light microscope and shape and morphology of colonies was observed. Shown are representative photomicrographs and the quantification of three independent experiments. Data are means±SEM (n=3).

(Data are Shown in FIG. 8)

Treprostinil rendered cells more susceptible to apoptosis (FIGS. 8A & B) or impeded their entry into and progression through the cell cycle (FIGS. 8C & D) or altered the ability of murine HSPCs to give rise to specific lineages (FIGS. 8E & F). As illustrated by the original dot plots (FIG. 8A) and summarized in FIG. 8B, the presence of viable, early apoptotic and dead cells was comparable and the number of annexin-V positive cells was not increased upon in vitro treatment with 30 μM forskolin and 10 μM Treprostinil. Similarly, the cell cycle distribution of asynchronously growing untreated human HSPCs and HSPCs maintained in the presence of Treprostinil and forskolin was comparable, regardless of whether HSPCs were exposed for 1 h or 24 h (cf. FIG. 8C for representative original histograms and FIG. 8D for averaged data). Importantly we also failed to detect any effect of Treprostinil and forskolin on the formation of myeloid and erythroid colonies: murine HSPCs were isolated form bone marrow, incubated for 1 h in the presence of Treprostinil and forskolin and resuspended in a methylcellulose containing medium with growth factors required for supporting the differentiation and growth of colony-forming units of the CFU-GM and of the BFU-E. After 10 days, the morphology (FIG. 8E) and the number of colonies was comparable (FIG. 8F).

Treprostinil Stimulates Migration of Human and Murine HSPCs Towards SDF-1/CXCL-12

As mentioned above, enhanced engraftment of dmPGE2-treated HSCs was attributed to effects on cell survival, proliferation and homing (10). Under our experimental conditions, in vitro treatment of murine and human HSPCs with Treprostinil and forskolin enhanced bone marrow reconstitution (see below and & FIG. 13), but did not alter cell viability or cell cycle progression in vitro (cf. FIG. 8).

The SDF-1/CXCR4 axis plays a major role in homing of HSCPs to the bone marrow niche. Thus we surmised that the beneficial action of Treprostinil resulted from enhanced engraftment of HSPCs through SDF-1/CXCR4-mediated effects.

Following data are shown in FIG. 9: In vitro pretreatment with Treprostinil and forskolin enhances expression of CXCR4 (A & B) and CD26/DPPIV (B). (A) RNA was isolated from human HSPCs, which had been incubated in the absence (untreated) or presence of the combination of 10 μM Treprostinil and 30 μM forskolin (Trep+Fsk) for 1 h. RNA prepared from the human PC3 cell line served as positive control. After reverse transcription, PCR-dependent amplification was done using primers listed in Table 1. Amplicons for CXCR4 were electrophoretically resolved on an agarose gel and visualized by ethidium bromide staining. The mRNA encoding β-actin was amplified as internal control. The data are representative of two additional experiments with similar results. (B, C) Human CD34+ cells (B) and mHSPCs were incubated either with 10 μM Treprostinil and 30 μM forskolin or vehicle controls (untreated) for 2 h, 4 h and 6 h. Subsequently, the samples were analysed for the expression of CXCR4 (B) and CD26 (FiC) by FACS. Shown is the percent of positive cells in ≥3 independent experiments (means±SEM; *P<0.05 vs. untreated control, ANOVA)

This conjecture was examined as follows: (i) prestimulation of human HSPCs with Treprostinil and forskolin raised mRNA levels of CXCR4 (FIG. 9A). This was also translated in enhanced expression of the CXCR4 protein (FIG. 9B). Interestingly, this was also accompanied by an upregulation of CD26/DPPIV (dipeptidylpeptides-IV), the enzyme which degrades the CXCR4 ligand SDF-1/CXCL12 (shown for murine HSPCs in FIG. 9C). (ii) The up-regulation of CXCR4 was resulted in enhanced migration of human (FIG. 10A) and murine HSPCs towards SDF-1 (FIG. 10B), respectively. (iii) This directed migration was specific, because it was blocked by the selective CXCR4-antagonist plerixafor/AMD3100 (FIG. 10C). Likewise, basal migration (i.e., random migration in the absence of SDF-1) was not enhanced by pretreating HSPCs with Treprostinil and forskolin (cf. first and third bar in FIGS. 10A & B).

FIG. 10 shows following data: In vitro pretreatment with Treprostinil and forskolin enhances the action of SDF-1 via CXCR4. Freshly isolated murine and human HPSCs were pretreated in vitro with either vehicle (open bars) or 10 μM Treprostinil and 30 μM forskolin (Trep+Fsk, closed bars) for 1 h at 37° C. followed by washing steps. A suspension (2×10⁵ cells in 0.1 mL medium containing growth factors) of human (A) or murine HSPCs (B, C) was added to the upper Transwell™ chamber and allowed to migrate towards SDF-1 (100 ng/mL in the lower chamber) for 4 h. Cells, which had migrated through the 5-μm filter, were counted. HSPCs were also incubated in the absence and presence of 10 μM AMD3100 (C). Data represent means±SEM from three independent experiments carried out in triplicate. The statistical comparison was done by ANOVA followed by Tukey's multiple comparison. (*, P<0.05; , P<0.01; * P<0.001).

Blockage of CXCR4 Blunts the Beneficial Effect of Treprostinil on Bone Marrow Transplantation The antagonism by AMD3100 was recapitulated in vivo: the bone marrow of lethally irradiated recipient mice was reconstituted with Treprostinil- and forskolin-pretreated murine HSPCs and the mice were subsequently administered subcutaneously the optimum dose of Treprostinil for 10 days. The concomitant administration of AMD3100 (3.3 mg kg$^{-1}$ 8 h$^{-1}$) blunted the beneficial action of Treprostinil such that all recipient mice eventually succumbed to bone marrow failure (FIG. 11). Thus, taken together, the observations indicate a mechanistic link between Treprostinil-induced cAMP accumulation, increased expression of CXCR4 and enhanced signalling by CXCR4 in Treprostinil-treated HSPCs. In addition, they also document that the action Treprostinil is contingent on CXCR4: if signalling by CXCR4 was blocked, the bone marrow was not engrafted and all animals died.

Inhibition of CD26/DPPIV by Vildagliptin Enhances Homing of and Bone Marrow Reconstitution by HPSCs Only Upon Sequential But Not Upon Concomitant Administration with Treprostinil Several chemokines are known to be degraded by CD26/DPPIV (dipeptidyl peptidase-IV). This is also true for SDF-1/CXCL12. Given the findings that the action of Treprostinil is mediated—at least in part—by induction of CXCR4 and it is contingent on CXCR4. Accordingly, an enhanced action of SDF-1/CXCL12 is predicted to be beneficial. In this context, it is worth to consider that the treatment with Treprostinil and forskolin also induced the expression of CD26, which was essentially undetectable in unstimulated HSPCs, but was detected in more than 10% of HSPCS, which had been stimulated with Treprostinil and forskolin (FIG. 9C). Several inhibitors of DPP-IV are available, their human pharmacology is well understood, they have been administered to millions of patients for many years in the treatment of type II diabetes. In fact, the vast majority of patients tolerate DPP-IV inhibitors without dangerous side effects.

Given that DPP-IV inhibitors may be a suitable combination partner for Treprostinil, we explored whether the DPP-IV inhibitor vildagliptin enhanced the action of Treprostinil. This was first tested in an approach, which measured the ability of injected HSPCs to home into the bone marrow: HSPCs harvested from the bone marrow of CD 45.1+ donor mice were injected into isogenic CD45.2 recipients. The animals were sacrificed after 16 h and the amount of CD45.1+ cells, which were retrieved from their bone marrows was quantified by FACS.

These experiments showed that (i) the sole pretreatment of HSPCs with the combination of Treprostinil+forskolin in vitro did not suffice to result in a statistically significant enhanced homing (cf. third bar and first bar in FIG. 12).

FIG. 12 shows that in vivo treatment of recipient mice with sole vildagliptin and Treprostinil but not with their combination increases homing of HSPCs, which had been preincubated with Treprostinil and forskolin. Murine HSPCs isolated from the bone marrow of CD 45.1+ donor mice were pretreated with either vehicle ("Untreated cells") or with Treprostinil and forskolin ("Treated cells") and transplanted ($2 \times 10^5$ cells per mouse) into lethally irradiated recipient C57Bl/6 (CD45.2+) mice via tail vein injection. The recipient mice were then divided in 7 groups. Mice in groups 1 and 2 had only untreated control cells, in addition mice in group 2 were treated in vivo with vildagliptin (Vil, 10 mg $kg^{-1}$/d). Mice allocated to group 3 received only in vitro-treated cells, those in group 4 were subjected—in addition—to in vivo Treprostinil (Trep, 0.15 mg $kg^{-1}$ 8 $h^{-1}$). Mice assigned to group 5 were administered a combined in vivo treatment with Treprostinil (0.15 mg kg-1 8 h-1) and AMD3100 (3.3 mg $kg^{-1}$ 8 $h^{-1}$). Mice in group 5 received in vivo both Treprostinil (0.15 mg $kg^{-1}$ 8 $h^{-1}$) and vildagliptin (10 mg $kg^{-1}$/d), and finally mice in group 6 were subjected to in vivo vildagliptin. The ability of CD45.1+cells to home into the bone marrow was assessed after 16 h by analysing the bone marrow of the recipients by FACS. Data are as means±SEM (n=3). Statistical comparisons were done by ANOVA followed by Tukey's multiple comparison. The combination in vitro pretreatment+in vivo vildagliptin (last bar, "+in vivo (Vil)") is statistically significant from all others (**, $p<0.01$). The 4th bar ("+in vivo Trep") differs in a statistically significant way from the first three bars, the 5th ("+in vivo (Trep+AMD 3100") and the 6th bar ("+in vivo (Trep+Vil)") (*, $p<0.05$).

Earlier observations had shown that in vitro pretreatment with dmPE2 enhanced homing of HSPCs (11). Thus, these findings again highlight the difference between a preincubation of HSPCs in dmPGE2 (11) and in the combination of Treprostinil and forskolin.

(ii) the pretreatment of HSPCs with the combination of Treprostinil+forskolin in vitro increased their homing into the bone marrow of recipient mice provided that these recipient mice were also treated with Treprostinil in vivo (cf fourth bar and third bar, FIG. 12).

(iii) enhanced homing resulting from the sequential in vitro pretreatment (with Treprostinil+forskolin) followed by in vivo administration of Treprostinil was abolished, if the recipient mice were administered the CXCR4 antagonist AMD3100/plerixafor (cf fourth bar and fifth bar, FIG. 12). This observation is consistent with the findings summarized above and in FIGS. 9, 10 and 11, which showed that the action of Treprostinil was contingent on the induction of CXCR4.

(iv) the sole in vivo administration of vildagliptin to recipient mice, which had received untreated HSPCs, did not enhance homing (cf second bar and first bar, FIG. 12).

(v) the in vivo administration of vildagliptin to recipient mice, which had received Treprostinil+forskolin-pretreated HSPCs and were subsequently administered Treprostinil in vivo, abrogated the homing effect of Treprostinil (cf. fourth bar and sixth bar, FIG. 12).

(vi) the most pronounced increase in homing was observed, if the HSPCs were pretreated in vitro with the combination of Treprostinil and forskolin and the recipient mice were administered vildagliptin; homing after this regimen exceeded all others including injection of Treprostinil+forskolin-pretreated HSPCs followed by administration of Treprostinil in vivo (cf. seventh bar and fourth bar, FIG. 12) or followed by administration of Treprostinil and vildagliptin in vivo (cf. seventh bar and sixth bar, FIG. 12).

Inhibition of CD26/DPPIV by Vildagliptin Enhances Bone Marrow Reconstitution by Treprostinil+Forskolin HPSCs Only Upon Sequential Administration Lethally irradiated BALB/c mice were rescued by the intravenous injection of $2*10^5$ $Lin^-$, $c-Kit^+$, $Sca1^+$ HSPCS. Under these conditions, the number of HSPCs is limiting such that all animals, which had been injected with untreated HSPCs die (solid line in FIG. 13). In contrast, 60% of the animals survived, if the HSPCs had been pretreated with the combination of Treprostinil and forskolin in vitro and the recipient animals were administered Treprostinil for 10 days (triangles/dotted lines in FIG. 13). Survival of recipient mice was augmented to 100%, if the HSPCs had been pretreated with the combination of Treprostinil and forskolin in vitro and the recipient animals were administered vildagliptin for 10 days (circles/dashed lines in FIG. 13). However, the combined administration of Treprostinil and vildagliptin resulted in a pronounced mutual antagonism: the vast majority of recipient died, if they were injected with HSPCs pretreated with the combination of Treprostinil and forskolin in vitro and were then administered Treprostinil and vildagliptin (squares/dotted lines in FIG. 13). These observations are consistent with the results of the homing assay summarized in FIG. 13; in other words two independent approaches documented mutual antagonism of Treprostinil and vildagliptin, when administered concomitantly in vivo, but synergism when applied in the right temporal sequence, i.e. in vitro pretreatment of HSPCs with Treprostinil+forskolin followed by in vivo administration of vildagliptin to recipient mice.

Blockage of CXCR4 by AMD3100/Plerixafor Antagonizes Blunts the Beneficial Effects of Vildagliptin on Survival of Recipient Mice, But AMD3100/Plerixafor Per Se Also Enhances Survival:

The working hypothesis underlying this project posits that administration of vildagliptin to recipient mice, which received HSPCs pretreated with the combination of forskolin+Treprostinil, because the breakdown of SDF-1/CXCL12 is inhibited and thus signalling via upregulated CXCR4 enhanced. If this was the case, the action of vildagliptin ought to be blunted by simultaneous administration of AMD3100/plerixafor. An experiment was done with seven groups of recipient BALB/c mice (5/group). Several of these groups were internal controls, which were included to verify that earlier findings were recapitulated. All mice received HSPCs, which had been pretreated with the combination of Treprostinil and forskolin in vitro prior to their injection via the tail vein. The number of HSPCs was limiting ($2*10^5$/mouse in BALB/c) such that sole injection of pretreated HSPCs did not suffice to rescue the recipients. Recipient mice, which were injected vildagliptin fared best; their survival was better than in the group, which had been administered Treprostinil (data from FIG. 11, see below). In addition, the animals, which were administered the combination of Treprostinil and vildagliptin did poorly; thus these observations recapitulate the results shown in FIG. 13. Survival of recipients, which had received the combination of vildagliptin and AMD3100/plerixafor, was lower than that of animals treated with vildagliptin alone. Thus, the action of vildagliptin can—at least in part—be accounted for by enhanced signalling of SDF-1/CXCL12 via CXCR4. It is stressed that all conditions were tested in parallel, thus a comparison is legitimate.

Conclusions:

The major findings can be summarized as follows:

(i) Treprostinil differs from dmPGE2, because Treprostinil activates $G_s$-coupled prostanoid receptors in (murine and human) HSPCs, dmPGE2 also activates $G_i$-coupled EP3 receptors, which are also present on HSPCs. Accordingly, sole in vitro treatment with Treprostinil (in combination with forskolin) does not enhance proliferation and survival of HSPCs in vitro (FIG. 8) nor their homing to the bone marrow in vivo (FIG. 11). This is in contrast to the published data for dmPGE2 (11). Homing is only enhanced, if the recipient animals are continuously treated with Treprostinil in vivo (FIG. 12).

(ii) The action of Treprostinil is—at least in part—contingent on the induction of CXCR4 (FIG. 9) and the resulting enhanced signalling of SDF-1/CXCL12 via CXCR4. This was documented in vitro by showing enhanced migration (chemotaxis) of Treprostinil+forskolin-pretreated HSPCs towards SDF1 (FIG. 10A, B), by blockage of this effect with the CXCR4 antagonist AMD3100/plerixafor (FIG. 10C), and in vivo by demonstrating inhibition by AMD3100/plerixafor of Treprostinil-induced enhanced homing (FIG. 12) and bone marrow engraftment/survival of recipient mice (FIG. 11).

(iii) Inhibition of CD26/DPP-IV does per se not affect homing of HSPCs to the bone marrow but synergizes with Treprostinil provided that the HSOPCs are first exposed to Treprostinil and forskolin in vitro and then to vildagliptin in vivo (FIG. 12). If the two compounds are administered simultaneously in vivo, there is mutual antagonism. This synergism and mutual antagonism was recapitulated in independent experiments, where engraftment of HSPCs rather than their homing was tested, i.e., the capacity of HSPCs to reconstitute the bone marrow in lethally irradiated recipient mice and thus to support their survival (FIG. 13).

FIG. 13 shows that sole in vivo administration of the DPP-IV inhibitor vildagliptin increases the beneficial effect of in vitro treatment of HSPCs with Treprostinil and forskolin on the survival rate in recipient mice. Murine HPSCs isolated from donor BALB/c mice were treated in vitro with 10 µM Treprostinil and 30 µM forskolin or vehicle (solid line) for 1 h at 37° C. After washing, $2 \times 10^5$ cells were injected into lethally irradiated (10 Gy) recipient BALB/c mice. The group of mice, which received vehicle-treated HSPCs, did not receive any additional treatment in vivo and served as control for irradiation (solid line, n=19): they all died due to bone marrow failure. Another group of mice (dotted lines/triangles; n=20) received HSPCs pretreated with 10 µM Treprostinil and 30 µM forskolin, and were also treated in vivo with Treprostinil (0.15 mg kg–1 8 h–1). The next group of mice (dotted lines/squares; n=20) again received in vitro HSPCs pretreated with forskolin+Treprostinil and were further treated in vivo with both Treprostinil (0.15 mg $kg^{-1}$ 8 $h^{-1}$) and vildagliptin (10 mg/kg/24 h). Finally, a group of mice (dashed lines/circles; n=20) received in vitro HSPCs pretreated with forskolin+Treprostinil and were treated in vivo with vildagliptin (10 mg kg–1 per day). In vivo treatment was done by subcutaneous injections, it was initiated directly after transplantation and continued for 10 days. Survival curves were compared by the log rank test; the difference between the three treatment conditions is statistically significant (p<0.01).

This surprising finding is difficult to understand, but it highlights the importance of the sequence of signals: the Treprostinil-provided $G_s$-dependent signal must precede the $G_i/G_q$-dependent signal generated by SDF-1/CXCL12 via CXCR4.

(iv) In vivo AMD3100/plerixafor antagonizes the beneficial effect of both, administration of Treprostinil and of vildagliptin. This antagonism is to be predicted, because Treprostinil induces CXCR4 and vildagliptin blocks the enzyme that degrades SDF-1/CXCL12. Thus both manipulations result in enhanced signalling via CXCR4, which is blocked by AMD3100/plerixafor. This observation highlights the importance of providing the right cues to the transplanted HSPCs in a sequential order (see above point (iii)). In addition, we noted previously that, in vivo, the dose-response-curve for Treprostinil was bell-shaped, i.e. higher doses were less beneficial in promoting bone marrow engraftment than the standard dose used in the current experiments. This may be due to the presence of EP4 receptors on the cells lining the endo-ostal niche, stimulation of which may counteract the actions of prostanoids on engraftment of HSPCs (15). Likewise, it is conceivable that SDF1/CXCL12 also exerts complex actions on the endostal niche, which may both, favour and impede bone marrow reconstitution depending on the signalling context.

Based on these findings, it can be concluded that (i) the in vitro pretreatment of HSPCs with the combination of Treprostinil and forskolin can be either combined with in vivo administration of Treprostinil or of vildagliptin to enhance bone marrow reconstitution.

(ii) the simultaneous application combination of both compounds (i.e., Treprostinil and vildagliptin) results in mutual antagonism and is thus of less value. However, it is conceivable that a sequential regimen, where vildagliptin and Treprostinil are administered in an alternating scheme, may be useful.

REFERENCES

1. Aronoff D M, Peres C M, Serezani C H, Ballinger M N, Carstens J K, Coleman N, Moore B B, Peebles R S, Faccioli L H, Peters-Golden M (2007) Synthetic prostacyclin analogs differentially regulate macrophage function via distinct analog-receptor binding specificities. *J. Immunol.* 178:1628-1634.
2. Whittle B J, Silverstein A M, Mottola D M, Clapp L H (2012) Binding and activity of the prostacyclin receptor (IP) agonists, Treprostinil and iloprost, at human prostanoid receptors: Treprostinil is a potent DP1 and EP2 agonist. *Biochem. Pharmacol.* 84:68-75.
3. Taschner S, Koesters C, Platzer B, Jorgl A, Ellmeier W, Benesch T, Strobl H (2007) Down-regulation of RXRalpha expression is essential for neutrophil development from granulocyte/monocyte progenitors. *Blood* 109:971-979.
4. Johnson R A, Alvarez, R, Salomon Y (1994) Determination of adenylyl cyclase catalytic activity using single and double chromatographic procedures. Methods in Enzymology 238:31-56
5. Tesmer J J, Sunahara R K, Gilman A G, Sprang S R (1997) Crystal structure of the catalytic domains of adenylyl cyclase in a complex with Gsα.GTPγS. *Science* 278: 1907-1916.
6. Sunahara R K, Dessauer C W, Gilman A G (1996) Complexity and diversity of mammalian adenylyl cyclases. *Annu. Rev. Pharmacol. Toxicol.* 36:461-480.
7. Kudlacek O, Mitterauer T, Nanoff C, Hohenegger M, Tang W J, Freissmuth M, Kleuss C (2001) Inhibition of adenylyl and guanylyl cyclase isoforms by the antiviral drug foscarnet. *J. Biol. Chem.* 276:3010-3016
8. Woodward D F, Jones R L and Narumiya S (2011) International Union of Basic and Clinical Pharmacology. LXXXIII: classification of prostanoid receptors, updating 15 years of progress. Pharmacol Rev 63:471-538.
9. Kiriyama M, Ushikubi F, Kobayashi T, Hirata M, Sugimoto Y, Narumiya S (1997) Ligand binding specificities of the eight types and subtypes of the mouse prostanoid receptors expressed in Chinese hamster ovary cells. *Br. J. Pharmacol.* 122:217-224
10. Insel P A, Zhang L, Murray F, Yokouchi H and Zambon A C (2012) Cyclic AMP is both a pro-apoptotic and anti-apoptotic second messenger. Acta Physiol (Oxf) 204: 277-287.
11. Hoggatt J, Singh P, Sampath J and Pelus L M (2009) Prostaglandin E2 enhances hematopoietic stem cell homing, survival, and proliferation. Blood 113:5444-5455.
12. Jia S, Roberts T M, Zhao J J (2009) Should individual PI3 kinase isoforms be targeted in cancer? Curr Opin Cell Biol. 21:199-208.
13. Zhang J, Zou F, Tang J, Zhang Q, Gong Y, Wang Q, Shen Y, Xiong L, Breyer R M, Lazarus M, Funk C D, Yu Y (2013) Cyclooxygenase-2-derived prostaglandin $E_2$ promotes injury-induced vascular neointimal hyperplasia through the E-prostanoid 3 receptor. Circ Res. 113:104-114.
14. Kang Y, Chen B J, Deoliveira D, Mito J, Chao N J (2010) Selective enhancement of donor hematopoietic cell engraftment by the CXCR4 antagonist AMD3100 in a mouse transplantation model. PLoS One 28; 5(6):e11316.
15. Hoggatt J, Mohammad K S, Singh P, Hoggatt A F, Chitteti B R, Speth J M, Hu P, Poteat B A, Stilger K N, Ferraro F, Silberstein L, Wong F K, Farag S S, Czader M, Milne G L, Breyer R M, Serezani C H, Scadden D T, Guise T A, Srour E F and Pelus L M (2013) Differential stem- and progenitor-cell trafficking by prostaglandin E2. *Nature* 495:365-369.

---

The invention claimed is:

1. A method of treating a subject who has received a haematopoetic stem cell transplant comprising haematopoetic stem cells and/or progenitor cells, comprising administering an inhibitor of dipeptidyl peptidase IV (DPP-IV) to the subject, wherein the inhibitor of DPP-IV is vildagliptin, wherein said haematopoetic stem cells and/or progenitor cells are treated in vitro before transplantation with a prostacyclin analogue and a cAMP enhancer to enhance engraftment, and wherein the prostacyclin analogue is selected from the group consisting of treprostinil, acid derivatives of treprostinil, isomers of treprostinil, and pharmaceutically acceptable salts thereof, and wherein the DPP-IV inhibitor is administered for a period of at least 1 day after haematopoetic stem cell transplantation.

2. The method of claim 1, wherein said prostacyclin analogue is treprostinil.

3. The method of claim 1, wherein said cAMP enhancer is forskolin.

4. The method of claim 1, wherein the haematopoetic stem cells are treated in vitro with treprostinil and forskolin.

5. The method of claim 1, wherein the DPP-IV inhibitor is administered between 5 and 24 hours before haematopoetic stem cell transplantation.

6. The method of claim 5, wherein the DPP-IV inhibitor is administered between 10 and 15 hours before the haematopoetic stem cell transplantation.

7. The method of claim 1, wherein the DPP-IV inhibitor is administered for a period of between 1 and 4 days after haematopoetic stem cell transplantation.

8. The method of claim 7, wherein the DPP-IV inhibitor is administered for a period of between 2 and 3 days after the haematopoetic stem cell transplantation.

9. The method of claim 1, wherein the subject has bone marrow disease.

10. The method of claim 9, wherein the bone marrow disease is selected from the group consisting of leukemia, a defect of the blood cell compartment, and a bone marrow disease induced by chemotherapy or irradiation.

11. The method of claim 10, wherein said defect of the blood cell compartment is a hemoglobinopathy, a defect in neutrophil granulocyte function, or a defect in T- and/or B-lymphocytes.

12. A method for enhancing the engraftment capabilities of haematopoetic cells, comprising the sequential steps of:
   a) providing a sample of haematopoetic stem cells or progenitor cells,
   b) administering an effective amount of a prostacyclin analogue and a cAMP enhancer to said cells, wherein the prostacyclin analogue is selected from the group consisting of treprostinil, acid derivatives of treprostinil, isomers of treprostinil, and pharmaceutically acceptable salts thereof,
   c) incubating said mixture for a period of time sufficient to stimulate G alphas-signaling in said cells,
   d) isolating said cells,
   e) transplanting said cells into an individual in need thereof, and
   f) administering to said individual an effective amount of a dipeptidyl peptidase IV (DPP-IV) inhibitor for a period of at least 1 day after haematopoetic stem cell transplantation, wherein the DPP-IV inhibitor is vildagliptin.

13. The method according to claim 12, wherein said stem cells or progenitor cells are derived from cord blood, donor bone marrow, or placenta.

\* \* \* \* \*